United States Patent [19]
Grundler

[11] Patent Number: 6,043,242
[45] Date of Patent: Mar. 28, 2000

[54] IMIDAZOPYRIDAZINES

[75] Inventor: Gerhard Grundler, Constance, Germany

[73] Assignee: Byk Gulden Lomberg Chemische Fabrik GmbH, Constance, Germany

[21] Appl. No.: 09/319,937

[22] PCT Filed: Dec. 18, 1997

[86] PCT No.: PCT/EP97/07133

§ 371 Date: Jun. 18, 1999

§ 102(e) Date: Jun. 18, 1999

[87] PCT Pub. No.: WO98/28299

PCT Pub. Date: Jul. 2, 1998

[30] Foreign Application Priority Data

Dec. 20, 1996 [DE] Germany ............ 196 53 375
Feb. 4, 1997 [EP] European Pat. Off. ............ 97101668

[51] Int. Cl.[7] ............ C07D 487/04; A61K 31/445
[52] U.S. Cl. ............ 514/241; 514/242; 514/248; 544/236; 544/181; 544/182
[58] Field of Search ............ 544/236, 182, 544/185; 514/248, 241, 242

[56] References Cited

U.S. PATENT DOCUMENTS 4,569,932  2/1986  Moran et al. ............ 514/248

FOREIGN PATENT DOCUMENTS 381132  8/1990  European Pat. Off. .
632040  1/1995  European Pat. Off. .

OTHER PUBLICATIONS

Kuwahara et al. Chem. Pharm. Bull., 43(9)), pp. 1511–1515, 1995.

*Primary Examiner*—Mukund J. Shah
*Assistant Examiner*—Beby Jayaram
*Attorney, Agent, or Firm*—Jacobson, Price, Holman & Stern, PLLC

[57] ABSTRACT

Compounds of formula (I)

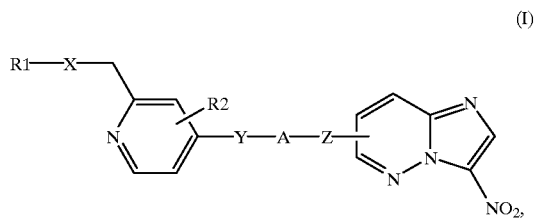

in which the substituents and symbols have the meanings indicated in the description, are suitable for controlling Helicobacter bacteria.

11 Claims, No Drawings

IMIDAZOPYRIDAZINES

This application is a 371 of PCT/EP97/07133 filed Dec. 18, 1997.

FIELD OF APPLICATION OF THE INVENTION

The invention relates to compounds which are intended to be used in the pharmaceutical industry as active compounds for the production of medicaments.

KNOWN TECHNICAL BACKGROUND

European Patent Application 632 040 describes imidazole derivatives which are intended to have an antibacterial action.

DESCRIPTION OF THE INVENTION

The invention relates to compounds of the formula I

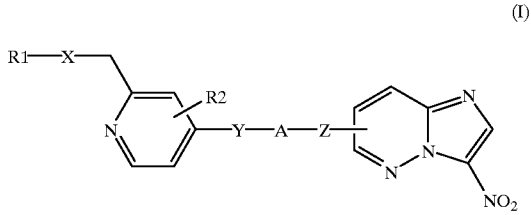

in which
R1 is hydrogen, 1–4C-alkyl, 1–4C-alkyl substituted by R11, 1–4C-alkylcarbonyl, 1–4C-alkoxycarbonyl, sulfo (—SO$_3$H) or a cyclic system or bicyclic system substituted by R11 and R12, which is selected from the group consisting of pyrrole, furan, thiophene, pyrazole, imidazole, imidazoline, oxazole, isoxazole, thiazole, thiazoline, isothiazole, triazole, oxadiazole, thiadiazole, thiadiazole-1-oxide, tetrazole, hexopyranoses, benzene, pyridine, pyridine-N-oxide, pyridazine, pyrimidine, pyrazine, triazine, naphthalene, quinoline, quinazoline, quinoxaline, benzimidazole, benzoxazole, benzothiazole, thiazolopyridine and imidazopyridine,
where
  R11 is hydrogen, 1–4C-alkyl, 3–7C-cycloalkyl, 1–4C-alkoxy, 1–4C-alkoxy-1–4C-alkoxy, 1–4C-alkylcarbonyl, amino, 1–4C-alkylcarbonyl-amino, halogen, trifluoromethyl, trifluoro-methoxy, hydroxyl, carboxyl, 1–4C-alkoxycarbonyl, 1–4C-alkylthio, 1–4C-alkylsulfinyl, 1–4C-alkylsulfonyl, sulfo (—SO$_3$H), nitro, guanidino, phenyl, phenyl substituted by R111, pyridyl, pyridyl substituted by R 111, imidazolyldione, thiazolyl, 1–4C-alkyl substituted by R111, —N(R112)R113 or —CO—N(R112)R113 and
  R12 is hydrogen, 1–4C-alkyl, 1–4C-alkoxy, halogen, amino, hydroxyl, phenyl or trifluoromethyl,
  where
    R111 is hydroxyl, 1–4C-alkyl, 1–4C-alkoxy, carboxyl, 1–4C-alkoxycarbonyl, halogen, aminosulfonyl or —N(R112)R113,
    R112 is hydrogen, 1–4C-alkyl, formyl, 1–4C-alkylcarbonyl or 1–4C-alkoxycarbonyl and
    R113 is hydrogen or 1–4C-alkyl, or where
    R112 and R113, together and including the nitrogen atom to which both are bonded, are a piperidino or morpholino radical,
R2 is hydrogen, 1–4C-al kyl or halogen, A is 2–7C-alkylene,
X is a bonding dash, O (oxygen) or S (sulfur),
Y is O (oxygen), S (sulfur) or N-1–4C-alkyl and
Z is O (oxygen) or S (sulfur),
and the salts of these compounds and their N-oxides and also the salts of the N-oxides.

1–4C-alkyl represents straight-chain or branched alkyl radicals having 1 to 4 carbon atoms. Examples which may be mentioned are the butyl, isobutyl, sec-butyl, tert-butyl, propyl, isopropyl, ethyl and methyl radicals.

1–4C-alkylcarbonyl represents a radical which, in addition to the carbonyl group, contains one of the abovementioned 1–4C-alkyl radicals. An example which may be mentioned is the acetyl radical.

1–4C-alkoxy represents a radical which, in addition to the oxygen atom, contains one of the abovementioned 1–4C-alkyl radicals. Examples which may be mentioned are the methoxy and ethoxy radicals.

1–4C-alkoxycarbonyl represents a radical which, in addition to the carbonyl group, contains one of the abovementioned 1–4C-alkoxy radicals. Examples which may be mentioned are the methoxycarbonyl and the ethoxycarbonyl radicals.

Hexopyranoses in the sense of the present invention are hexoses (such as, for example, galactose, mannose or in particular glucose), which are present in pyranoside form and which are bonded glycosidically to the rest of the molecule. Glucopyranose is particularly preferred.

3–7C-cycloalkyl represents the cyclopropyl, cyclobutyl, cyclopentyl, cyclohexyl and cycloheptyl radicals.

1–4C-alkoxy-1–4C-alkoxy represents 1–4C-alkoxy which is substituted by 1–4C-alkoxy. Examples which may be mentioned are the methoxyethoxy, the ethoxyethoxy and the methoxypropoxy radicals.

1–4C-alkylcarbonylamino represents amino which is substituted by one of the abovementioned 1–4C-alkylcarbonyl radicals. An example which may be mentioned is the acetylamino radical (acetamido radical).

1–4C-alkylthio represents a radical which, in addition to the sulfur atom, contains one of the abovementioned 1–4C-alkyl radicals. Examples which may be mentioned are the methylthio and the ethylthio radicals.

1–4C-alkylsulfinyl represents a radical which, in addition to the sulfinyl group (—SO—), contains one of the abovementioned 1–4C-alkyl radicals. Examples which may be mentioned are the methylsulfinyl and the ethylsulfinyl radicals.

1–4C-alkylsulfonyl represents a radical which, in addition to the sulfonyl group (—SO$_2$—), contains one of the abovementioned 1–4C-alkyl radicals. Examples which may be mentioned are the methylsulfonyl and the ethylsulfonyl radicals.

Exemplary 1–4C-alkyl radicals substituted by R111 which may be mentioned are the 2-methoxycarbonylethyl, the 2-ethoxycarbonylethyl, the methoxycarbonylmethyl, the carboxymethyl, the 2-hydroxyethyl, the methoxymethyl, the 2-methoxyethyl, the dimethylaminomethyl and the 2-dimethylaminoethyl radicals.

2–7C-.alkylene represents straight-chain or branched alkylene radicals having 2 to 7 carbon atoms. Examples which may be mentioned are the heptylene, isoheptylene (2-methylhexylene), hexylene, isohexylene (2-methylpentylene), neohexylene (2,2-dimethylbutylene), pentylene, isopentylene (3-methylbutylene), neopentylene (2,2-dimethylpropylene), butylene, isobutylene, sec-butylene, tert-butylene, propylene, isopropylene and ethylene radicals. The ethylene (—CH$_2$CH$_2$—), the butylene (—CH$_2$CH$_2$CH$_2$CH$_2$—) and in particular the propylene (—CH$_2$CH$_2$CH$_2$—) radicals are preferred.

The cyclic systems or bicyclic systems R1 can be linked to X through any sensible position. On the other hand, the substituents R11 and R12 in the cyclic systems or bicyclic systems R1 can also be bonded at any sensible position. Exemplary radicals R1 which may be mentioned are:

2-pyrrolyl, 3-pyrrolyl, 1-methyl-3-pyrrolyl, 2-furyl, 3-furyl, 2-methyl-3-furyl, 2-dimethylaminomethyl-5-methyl-3-furyl, 5-(2-dimethylaminoethyl)-2-furyl, 5-methyl-2-furyl, 2-thienyl, 3-thienyl, 5-chloro-2-thienyl, 3-pyrazolyl, 4-pyrazolyl, 1-methyl-3-pyrazolyl, 1-(2-dimethylaminoethyl)-3-pyrazolyl, 2-imidazolyl, 1-methyl-2-imidazolyl, 5-nitro-1-imidazolyl, 2-methyl-5-nitro-1-imidazolyl, 4,5-diphenyl-1-imidazolyl, 2-imidazolinyl, 2-oxazolyl, 4-oxazolyl, 4,5-dimethyl-2-oxazolyl, 4-isoxazolyl, 5-isoxazolyl, 3,5-dimethyl-4-isoxazolyl, 2-thiazolyl, 4,5-dimethyl-2-thiazolyl, 4-methyl-5-carboxymethyl-2-thiazolyl, 3,4-dimethyl-2-thiazolyl, 2-thiazolinyl, 3-isothiazolyl, 1,2,3-triazol-4-yl, 1,2,4-triazol-3-yl, 1-methyl-1,2,3-triazol-4-yl, 1-methyl-1,2,4-triazol-3-yl, 4-methyl-1,2,4-triazol-3-yl, 1-(2-dimethylaminoethyl)-1,2,3-triazol-4-yl, 3-amino-1,2,4-triazol-5-yl, 4-methyl-5-trifluoromethyl-1,2,4-triazol-3-yl, 5-methyl-1,2,4-triazol-3-yl, 1,3,4-oxadiazol-2-yl, 5-methyl-1,3,4-oxadiazol-2-yl, 5-phenyl-1,3,4-oxadiazol-2-yl, 3-phenyl-1,2,4-oxadiazol-5-yl, 1,2,5-thiadiazol-4-yl, 1,2,5-thiadiazol-4-yl-1-oxide, 1,3,4-thiadiazol-2-yl, 1,2,3-thiadiazol-2-yl, 5-methyl-1,3,4-thiadiazol-2-yl, 2-amino-1,3,4-thiadiazol-5-yl, 5-amino-1,3,4-thiadiazol-2-yl, 5-trifluoromethyl-1,3,4-thiadiazol-2-yl, 5-tetrazolyl, 1-methyl-5-tetrazolyl, 1-phenyl-5-tetrazolyl, 1-(2-dimethylaminoethyl)-5-tetrazolyl, 1-(4-aminosulfonylphenyl)-5-tetrazolyl, 1-carboxymethyl-5-tetrazolyl, 1-(2-hydroxyethyl)-5-tetrazolyl, phenyl, 2-amino-4-chlorophenyl, 2-amino-4-trifluoromethylphenyl, 4-acetamidophenyl, 2-aminophenyl, 3-aminophenyl, 4-aminophenyl, 2-bromophenyl, 3-bromophenyl, 4-bromophenyl, 2-chlorophenyl, 3-chlorophenyl, 4-chlorophenyl, 2,5-dichlorophenyl, 2,6-dichlorophenyl, 3,4-dichlorophenyl, 2,3-dichlorophenyl, 2,4-dichlorophenyl, 3,5-dichlorophenyl, 2-chloro-6-methylphenyl, 4-chloro-2-methylphenyl, 2-chloro-4-fluorophenyl, 3-chloro-4-fluorophenyl, 2,4-dimethylphenyl, 2,5-dimethylphenyl, 2,6-dimethylphenyl, 3,4-dimethylphenyl, 3,5-dimethylphenyl, 2-ethylphenyl, 4-ethylphenyl, 2-fluorophenyl, 4-fluorophenyl, 3-fluorophenyl, 2-hydroxyphenyl, 4-hydroxyphenyl, 2-hydroxymethylphenyl, 4-hydroxymethylphenyl, 2-isopropylphenyl, 4-isopropylphenyl, 2-methoxyphenyl, 3-methoxyphenyl, 4-methoxyphenyl, 2,5-dimethoxyphenyl, 3,4-dimethoxyphenyl, 2-carboxyphenyl, 4-carboxyphenyl, 2-methoxycarbonylphenyl, 4-nitrophenyl, 2-nitro-4-trifluoromethylphenyl, 2-methylphenyl, 3-methylphenyl, 4-methylphenyl, 4-tert-butylphenyl, 4-methylthiophenyl, 3-dimethylaminomethylphenyl, 3-piperidinomethylphenyl, 3-carboxymethylphenyl, 4-carboxyethylphenyl, 3-trifluoromethylphenyl, 4-trifluoromethylphenyl, 2-trifluoromethylphenyl, 2-trifluoromethoxyphenyl, 4-trifluoromethoxyphenyl, 2-pyridyl, 4-pyridyl, 3-hydroxy-2-pyridyl, 3-carboxy-2-pyridyl, 5-nitro-2-pyridyl, 3-amino-6-methoxy-2-pyridyl, 5-trifluoromethyl-2-pyridyl, 3-chloro-5-trifluoromethyl-2-pyridyl, 3-trifluoromethyl-2-pyridyl, 2-pyridyl-1-oxide, 2-pyrimidinyl, 2-amino-4-pyrimidinyl, 4-amino-2-pyrimidinyl, 2,4-diamino-6-pyrimidinyl, 4-amino-6-hydroxy-2-pyrimidinyl, 4,6-dihydroxy-2-pyrimidinyl, 2,4-dihydroxy-5-pyrimidinyl, 2-amino-4-ethylamino-6-pyrimidinyl, 4-methyl-2-pyrimidinyl, 4,6-dimethyl-2-pyrimidinyl, 2-ethylthio-6-methyl-4-pyrimidinyl, 2-hydroxy-4-pyrimidinyl, 5-methoxy-4-pyrimidinyl, 4-trifluoromethyl-2-pyrimidinyl, 1,3,4-triazin-2-yl, 5,6-dihydroxy-1,3,4-triazin-2-yl, 1-naphthyl, 2-naphthyl, 2-quinolyl, 8-quinolyl, 7-trifluoromethyl-4-quinolyl, 4-quinazolyl, 4-hydroxy-2-quinazolyl, 2-quinoxalyl, 2-benzimidazolyl, 5-methyl-2-benzimidazolyl, 5-nitro-2-benzimidazolyl, 5-sulfo-2-benzimidazolyl, 5-methoxy-2-benzimidazolyl, 5-(2-thiazolyl)-2-benzimidazolyl, 5-methylthio-2-benzimidazolyl, 5-methylsulfonyl-2-benzimidazolyl, 2-benzoxazolyl, 2-benzothiazolyl, 5-chloro-2-benzothiazolyl, 6-nitro-2-benzothiazolyl, 6-amino-2-benzothiazolyl, 6-methoxy-2-benzothiazolyl, 6-ethoxy-2-benzothiazolyl and 2-imidazopyridyl.

Exemplary substituents R1 (if they are 1–4C-alkyl substituted by R11) which may be furthermore mentioned are the radicals:

2-hydroxyethyl, 2-carboxyethyl, 2-aminoethyl, 2-dimethylaminoethyl, 2-diethylaminoethyl, 2-acetylaminoethyl, cyclopropylmethyl, 2-oxopropyl and 2,2,2-trifluoroethyl.

Suitable salts of compounds of the formula I are both acid addition salts and salts with bases. Among the acid addition salts, particular mention may be made of the pharmacologically tolerable salts of the inorganic and organic acids customarily used in pharmacy. Pharmacologically intolerable salts which can be initially obtained as process products, for example, in the preparation of the compounds according to the invention on an industrial scale, are converted into pharmacologically tolerable salts by processes known to the person skilled in the art. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid, or 3-hydroxy-2-naphthoic acid, where the salts are employed in the salt preparation (depending on whether a mono- or polybasic acid is concerned and depending on which salt is desired) in an equimolar quantitative ratio or one differing therefrom.

For compounds of the formula I having (a) carboxyl group(s) or having (a) sulfo group(s), suitable salts are also salts with bases. Examples of salts with bases which may be mentioned are lithium, sodium, potassium, calcium, aluminum, magnesium, titanium, ammonium, meglumine or guanidinium salts, where here too the bases are employed in the salt preparation in an equimolar quantitative ratio or one differing therefrom.

One embodiment (embodiment a) of the invention are compounds of the formula I in which X is a bonding dash and R1 is hydrogen, 1–4C-alkyl or 1–4C-alkyl substituted by R11.

A further embodiment (embodiment b) of the invention are compounds of the formula I in which X is O (oxygen) and R1 is hydrogen or 1–4C-alkyl.

A further embodiment (embodiment c) of the invention are compounds of the formula I in which X is S (sulfur).

A further embodiment (embodiment d) of the invention are compounds of the formula I in which Y is O (oxygen) and Z is O (oxygen).

A further embodiment (embodiment e) of the invention are compounds of the formula I in which Y is S (sulfur) and Z is S (sulfur).

A further embodiment (embodiment f) of the invention are compounds of the formula I in which Y is N-1-4C-alkyl and Z is S (sulfur).

A further embodiment (embodiment g) of the invention are compounds of the formula I in which Y is O (oxygen) and Z is S (sulfur). Preferred compounds of the formula I are those in which the substituent R2 is in the 3-position in the pyridine ring.

Furthermore preferred compounds of the formula I are those in which the bridging member —Y—A—Z— to the pyridine ring is linked in position 6 to the 3-nitroimidazo[1,2-b]pyridazine.

Preferred compounds according to the invention are thus those of the formula I*

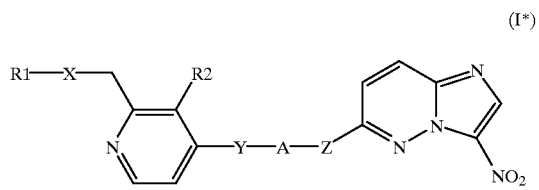

in which
R1, R2, A, X, Y and Z have the meanings indicated above, and the salts of these compounds and their N-oxides and also the salts of the N-oxides.

Furthermore preferred compounds of the formula I or of the formula I* are those in which A is ethylene or propylene.

Compounds to be emphasized are those of the formula I, in which

R1 is hydrogen, 1–4C-alkyl, 1–4C-alkyl substituted by R11, 1–4C-alkylcarbonyl, sulfo (—SO₃H) or a cyclic system or bicyclic system substituted by R11 and R12, which is selected from the group consisting of pyrrole, furan, thiophene, pyrazole, imidazole, imidazoline, oxazole, isoxazole, thiazole, thiazoline, isothiazole, triazole, oxadiazole, thiadiazole, thiadiazole-1-oxide, tetrazole, hexopyranoses, benzene, pyridine, pyridine-N-oxide, pyridazine, pyrimidine, pyrazine, naphthalene, quinoline, quinazoline, quinoxaline, benzimidazole, benzothiazole, thiazolopyridine and imidazopyridine, where R11 is hydrogen, 1–4C-alkyl, 3–7C-cycloalkyl, 1–4C-alkoxy, 1–4C-alkoxy-1–4C-alkoxy, 1–4C-alkylcarbonyl, amino, 1–4C-alkylcarbonyl-amino, halogen, trifluoromethyl, trifluoro-methoxy, hydroxyl, carboxyl, 1–4C-alkoxycarbonyl, 1–4C-alkylthio, 1–4C-alkylsulfonyl, nitro, phenyl, phenyl substituted by R111, pyridyl, pyridyl substituted by R111, imidazolyidione, thiazolyl, 1–4C-alkyl substituted by R111, —N(R112)R113 or —CO—N(R112)R113 and R12 is hydrogen, 1–4C-alkyl, 1–4C-alkoxy, halogen, amino, hydroxyl or phenyl, where R111 is hydroxyl, 1–4C-alkyl, 1–4C-alkoxy, carboxyl, halogen, aminosulfonyl or —N(R112)R113, R112 is hydrogen, 1–4C-alkyl, 1–4C-alkylcarbonyl or 1–4C-alkoxycarbonyl and R113 is hydrogen or 1–4C-alkyl, R2 is hydrogen, 1–4C-alkyl or halogen,
A is 2–7C-alkylene,
X is a bonding dash, O (oxygen) or S (sulfur),
Y is O (oxygen), S (sulfur) or N-1–4C-alkyl and
Z is O (oxygen) or S (sulfur), and the salts of these compounds and their N-oxides and also the salts of the N-oxides.

Compounds particularly to be emphasized are those of the formula I
in which

R1 is hydrogen, 1–4C-alkyl, 1–4C-alkyl substituted by R11, 1–4C-alkylcarbonyl, sulfo (—SO₃H) or a cyclic system or bicyclic system substituted by R11 and R12, which is selected from the group consisting of imidazole, tetrazole, hexopyranoses, pyridine, pyridine-N-oxide, pyrimidine, benzimidazole and thiazolopyridine, where R11 is hydrogen, 1–4C-alkyl, 3–7C-cycloalkyl, 1–4C-alkoxy, 1–4C-alkoxy-1–4C-alkoxy, 1–4C-alkylcarbonyl, amino, halogen, trifluoromethyl, hydroxyl, carboxyl, 1–4C-alkoxycarbonyl, 1–4C-alkylthio, 1–4C-alkylsulfonyl, phenyl, phenyl substituted by R111, pyridyl, pyridyl substituted by R111, imidazolyidione, thiazolyl, 1–4C-alkyl substituted by R111 or —N(R112)R113 and R12 is hydrogen, 1–4C-alkyl, amino or hydroxyl, where R111 is hydroxyl, 1–4C-alkyl, 1–4C-alkoxy or —N(R112)R113, R112 is hydrogen, 1–4C-alkyl or 1–C-alkylcarbonyl and R113 is hydrogen or 1–4C-alkyl, R2 is hydrogen, 1–4C-alkyl or halogen,
A is 2–5C-alkylene,
X is a bonding dash, O (oxygen) or S (sulfur),
Y is O (oxygen), S (sulfur) or N-1–4C-alkyl and
Z is O (oxygen) or S (sulfur), and the salts of these compounds and their N-oxides and also the salts of the N-oxides.

Preferred compounds are those of the formula I,
in which

R1 is hydrogen, 1–4C-alkyl, 1–4C-alkyl substituted by R11, 1–4C-alkylcarbonyl, sulfo (—SO₃H) or a cyclic system or bicyclic system substituted by R11 and R12, which is selected from the group consisting of imidazole, tetrazole, pyridine, pyrimidine and benzimidazole, where R11 is hydrogen, 1–4C-alkyl, 1–4C-alkoxy, 1–4C-alkoxy-1–4C-alkoxy, 1–4C-alkylthio, 1–4C-alkylsulfonyl, phenyl, phenyl substituted by R111, pyridyl, pyridyl substituted by R111 or thiazolyl and R12 is hydrogen, where R111 is hydroxyl or 1–4C-alkyl, R2 is 1–4C-alkyl or halogen,
A is 2–4C-alkylene,
X is a bonding dash, O (oxygen) or S (sulfur),
Y is O (oxygen), S (sulfur) or N-1–4C-alkyl and
Z is O (oxygen) or S (sulfur), and the salts of these compounds and their N-oxides and also the salts of the N-oxides.

Exemplary compounds according to the invention are listed in the following tables, namely

TABLE 1

Compounds of the formula I* where X = bonding dash and with the following further meanings:

| R1 | R2       | Y         | A         | Z |
|----|----------|-----------|-----------|---|
| H  | methyl   | O         | ethylene  | O |
| H  | methyl   | O         | propylene | O |
| H  | chlorine | O         | ethylene  | O |
| H  | chlorine | O         | propylene | O |
| H  | methyl   | O         | ethylene  | S |
| H  | methyl   | O         | propylene | S |
| H  | chlorine | O         | ethylene  | S |
| H  | chlorine | O         | propylene | S |
| H  | methyl   | S         | ethylene  | S |
| H  | methyl   | S         | propylene | S |
| H  | chlorine | S         | ethylene  | S |
| H  | chlorine | S         | propylene | S |
| H  | methyl   | N-methyl  | ethylene  | S |
| H  | methyl   | N-methyl  | propylene | S |
| H  | chlorine | N-methyl  | ethylene  | S |
| H  | chlorine | N-methyl  | propylene | S |

TABLE 2

Compounds of the formula I* where X = O, Y = O, Z = O, A = ethylene and with the following further meanings:

| R1 | R2 |
|----|----|
| methoxyethoxyethyl | methyl |
| acetyl | methyl |
| 2-pyrimidinyl | methyl |
| 2-benzimidazolyl | methyl |
| H | methyl |
| methyl | methyl |
| methoxyethyl | methyl |
| 1-(4-hydroxyphenyl)-1H-tetrazol-5-yl | methyl |
| 4-pyridyl | methyl |
| 5-methylthio-benzimidazol-2-yl | methyl |
| 5-(thiazol-2-yl)-benzimidazol-2-yl | methyl |
| 5-methylsulfonyl-benzimidazol-2-yl | methyl |
| 1-phenyl-1H-tetrazol-5-yl | methyl |
| 1-(3-methyl-pyridin-2-yl)-1H-imidazol-2-yl | methyl |
| 1-(pyridin-2-yl)-1H-imidazol-2-yl | methyl |
| methoxyethoxyethyl | chlorine |
| acetyl | chlorine |
| 2-pyrimidinyl | chlorine |
| 2-benzimidazolyl | chlorine |
| H | chlorine |
| methyl | chlorine |
| methoxyethyl | chlorine |
| 1-(4-hydroxyphenyl)-1H-tetrazol-5-yl | chlorine |
| 4-pyridyl | chlorine |
| 5-methylthio-benzimidazol-2-yl | chlorine |
| 5-(thiazol-2-yl)-benzimidazol-2-yl | chlorine |
| 5-methylsulfonyl-benzimidazol-2-yl | chlorine |
| 1-phenyl-1H-tetrazol-5-yl | chlorine |
| 1-(3-methyl-pyridin-2-yl)-1H-imidazol-2-yl | chlorine |
| 1-(pyridin-2-yl)-1H-imidazol-2-yl | chlorine |

TABLE 3

Compounds of the formula I* where X = O, Y = O, Z = O, A = propylene and with the following further meanings:

| R1 | R2 |
|----|----|
| methoxyethoxyethyl | methyl |
| acetyl | methyl |
| 2-pyrimidinyl | methyl |
| 2-benzimidazolyl | methyl |
| H | methyl |
| methyl | methyl |
| methoxyethyl | methyl |
| 1-(4-hydroxyphenyl)-1H-tetrazol-5-yl | methyl |
| 4-pyridyl | methyl |
| 5-methylthio-benzimidazol-2-yl | methyl |
| 5-(thiazol-2-yl)-benzimidazol-2-yl | methyl |
| 5-methylsulfonyl-benzimidazol-2-yl | methyl |
| 1-phenyl-1H-tetrazol-5-yl | methyl |
| 1-(3-methyl-pyridin-2-yl)-1H-imidazol-2-yl | methyl |
| 1-(pyridin-2-yl)-1H-imidazol-2-yl | methyl |
| methoxyethoxyethyl | chlorine |
| acetyl | chlorine |
| 2-pyrimidinyl | chlorine |
| 2-benzimidazolyl | chlorine |
| H | chlorine |
| methyl | chlorine |
| methoxyethyl | chlorine |
| 1-(4-hydroxyphenyl)-1H-tetrazol-5-yl | chlorine |
| 4-pyridyl | chlorine |
| 5-methylthio-benzimidazol-2-yl | chlorine |
| 5-(thiazol-2-yl)-benzimidazol-2-yl | chlorine |
| 5-methylsulfonyl-benzimidazol-2-yl | chlorine |
| 1-phenyl-1H-tetrazol-5-yl | chlorine |
| 1-(3-methyl-pyridin-2-yl)-1H-imidazol-2-yl | chlorine |
| 1-(pyridin-2-yl)-1H-imidazol-2-yl | chlorine |

TABLE 4

Compounds of the formula I* where X = S, Y = O, Z = O, A = ethylene and with the following further meanings:

| R1 | R2 |
|----|----|
| methoxyethoxyethyl | methyl |
| acetyl | methyl |
| 2-pyrimidinyl | methyl |
| 2-benzimidazolyl | methyl |
| H | methyl |
| methyl | methyl |
| methoxyethyl | methyl |
| 1-(4-hydroxyphenyl)-1H-tetrazol-5-yl | methyl |
| 4-pyridyl | methyl |
| 5-methylthio-benzimidazol-2-yl | methyl |
| 5-(thiazol-2-yl)-benzimidazol-2-yl | methyl |
| 5-methylsulfonyl-benzimidazol-2-yl | methyl |
| 1-phenyl-1H-tetrazol-5-yl | methyl |
| 1-(3-methyl-pyridin-2-yl)-1H-imidazol-2-yl | methyl |
| 1-(pyridin-2-yl)-1H-imidazol-2-yl | methyl |
| methoxyethoxyethyl | chlorine |
| acetyl | chlorine |
| 2-pyrimidinyl | chlorine |
| 2-benzimidazolyl | chlorine |
| H | chlorine |
| methyl | chlorine |
| methoxyethyl | chlorine |
| 1-(4-hydroxyphenyl)-1H-tetrazol-5-yl | chlorine |
| 4-pyridyl | chlorine |
| 5-methylthio-benzimidazol-2-yl | chlorine |
| 5-(thiazol-2-yl)-benzimidazol-2-yl | chlorine |
| 5-methylsulfonyl-benzimidazol-2-yl | chlorine |
| 1-phenyl-1H-tetrazol-5-yl | chlorine |
| 1-(3-methyl-pyridin-2-yl)-1H-imidazol-2-yl | chlorine |
| 1-(pyridin-2-yl)-1H-imidazol-2-yl | chlorine |

TABLE 5

Compounds of the formula I* where X = S, Y = O, Z = O,
A = propylene and with the following further meanings:

| R1 | R2 |
|---|---|
| methoxyethoxyethyl | methyl |
| acetyl | methyl |
| 2-pyrimidinyl | methyl |
| 2-benzimidazolyl | methyl |
| H | methyl |
| methyl | methyl |
| methoxyethyl | methyl |
| 1-(4-hydroxyphenyl)-1H-tetrazol-5-yl | methyl |
| 4-pyridyl | methyl |
| 5-methylthio-benzimidazol-2-yl | methyl |
| 5-(thiazol-2-yl)-benzimidazol-2-yl | methyl |
| 5-methylsulfonyl-benzimidazol-2-yl | methyl |
| 1-phenyl-1H-tetrazol-5-yl | methyl |
| 1-(3-methyl-pyridin-2-yl)-1H-imidazol-2-yl | methyl |
| 1-(pyridin-2-yl)-1H-imidazol-2-yl | methyl |
| methoxyethoxyethyl | chlorine |
| acetyl | chlorine |
| 2-pyrimidinyl | chlorine |
| 2-benzimidazolyl | chlorine |
| H | chlorine |
| methyl | chlorine |
| methoxyethyl | chlorine |
| 1-(4-hydroxyphenyl)-1H-tetrazol-5-yl | chlorine |
| 4-pyridyl | chlorine |
| 5-methylthio-benzimidazol-2-yl | chlorine |
| 5-(thiazol-2-yl)-benzimidazol-2-yl | chlorine |
| 5-methylsulfonyl-benzimidazol-2-yl | chlorine |
| 1-phenyl-1H-tetrazol-5-yl | chlorine |
| 1-(3-methyl-pyridin-2-yl)-1H-imidazol-2-yl | chlorine |
| 1-(pyridin-2-yl)-1H-imidazol-2-yl | chlorine |

TABLE 6

Compounds of the formula I* where X = O, Y = O, Z = S,
A = ethylene and with the following further meanings:

| R1 | R2 |
|---|---|
| methoxyethoxyethyl | methyl |
| acetyl | methyl |
| 2-pyrimidinyl | methyl |
| 2-benzimidazolyl | methyl |
| H | methyl |
| methyl | methyl |
| methoxyethyl | methyl |
| 1-(4-hydroxyphenyl)-1H-tetrazol-5-yl | methyl |
| 4-pyridyl | methyl |
| 5-methylthio-benzimidazol-2-yl | methyl |
| 5-(thiazol-2-yl)-benzimidazol-2-yl | methyl |
| 5-methylsulfonyl-benzimidazol-2-yl | methyl |
| 1-phenyl-1H-tetrazol-5-yl | methyl |
| 1-(3-methyl-pyridin-2-yl)-1H-imidazol-2-yl | methyl |
| 1-(pyridin-2-yl)-1H-imidazol-2-yl | methyl |
| methoxyethoxyethyl | chlorine |
| acetyl | chlorine |
| 2-pyrimidinyl | chlorine |
| 2-benzimidazolyl | chlorine |
| H | chlorine |
| methyl | chlorine |
| methoxyethyl | chlorine |
| 1-(4-hydroxyphenyl)-1H-tetrazol-5-yl | chlorine |
| 4-pyridyl | chlorine |
| 5-methylthio-benzimidazol-2-yl | chlorine |
| 5-(thiazol-2-yl)-benzimidazol-2-yl | chlorine |
| 5-methylsulfonyl-benzimidazol-2-yl | chlorine |
| 1-phenyl-1H-tetrazol-5-yl | chlorine |
| 1-(3-methyl-pyridin-2-yl)-1H-imidazol-2-yl | chlorine |
| 1-(pyridin-2-yl)-1H-imidazol-2-yl | chlorine |

TABLE 7

Compounds of the formula I* where X = O, Y = O, Z = S,
A = propylene and with the following further meanings:

| R1 | R2 |
|---|---|
| methoxyethoxyethyl | methyl |
| acetyl | methyl |
| 2-pyrimidinyl | methyl |
| 2-benzimidazolyl | methyl |
| H | methyl |
| methyl | methyl |
| methoxyethyl | methyl |
| 1-(4-hydroxyphenyl)-1H-tetrazol-5-yl | methyl |
| 4-pyridyl | methyl |
| 5-methylthio-benzimidazol-2-yl | methyl |
| 5-(thiazol-2-yl)-benzimidazol-2-yl | methyl |
| 5-methylsulfonyl-benzimidazol-2-yl | methyl |
| 1-phenyl-1H-tetrazol-5-yl | methyl |
| 1-(3-methyl-pyridin-2-yl)-1H-imidazol-2-yl | methyl |
| 1-(pyridin-2-yl)-1H-imidazol-2-yl | methyl |
| methoxyethoxyethyl | chlorine |
| acetyl | chlorine |
| 2-pyrimidinyl | chlorine |
| 2-benzimidazolyl | chlorine |
| H | chlorine |
| methyl | chlorine |
| methoxyethyl | chlorine |
| 1-(4-hydroxyphenyl)-1H-tetrazol-5-yl | chlorine |
| 4-pyridyl | chlorine |
| 5-methylthio-benzimidazol-2-yl | chlorine |
| 5-(thiazol-2-yl)-benzimidazol-2-yl | chlorine |
| 5-methylsulfonyl-benzimidazol-2-yl | chlorine |
| 1-phenyl-1H-tetrazol-5-yl | chlorine |
| 1-(3-methyl-pyridin-2-yl)-1H-imidazol-2-yl | chlorine |
| 1-(pyridin-2-yl)-1H-imidazol-2-yl | chlorine |

TABLE 8

Compounds of the formula I* where X = S, Y = O, Z = S,
A = ethylene and with the following further meanings:

| R1 | R2 |
|---|---|
| methoxyethoxyethyl | methyl |
| acetyl | methyl |
| 2-pyrimidinyl | methyl |
| 2-benzimidazolyl | methyl |
| H | methyl |
| methyl | methyl |
| methoxyethyl | methyl |
| 1-(4-hydroxyphenyl)-1H-tetrazol-5-yl | methyl |
| 4-pyridyl | methyl |
| 5-methylthio-benzimidazol-2-yl | methyl |
| 5-(thiazol-2-yl)-benzimidazol-2-yl | methyl |
| 5-methylsulfonyl-benzimidazol-2-yl | methyl |
| 1-phenyl-1H-tetrazol-5-yl | methyl |
| 1-(3-methyl-pyridin-2-yl)-1H-imidazol-2-yl | methyl |
| 1-(pyridin-2-yl)-1H-imidazol-2-yl | methyl |
| methoxyethoxyethyl | chlorine |
| acetyl | chlorine |
| 2-pyrimidinyl | chlorine |
| 2-benzimidazolyl | chlorine |
| H | chlorine |
| methyl | chlorine |
| methoxyethyl | chlorine |
| 1-(4-hydroxyphenyl)-1H-tetrazol-5-yl | chlorine |
| 4-pyridyl | chlorine |
| 5-methylthio-benzimidazol-2-yl | chlorine |
| 5-(thiazol-2-yl)-benzimidazol-2-yl | chlorine |
| 5-methylsulfonyl-benzimidazol-2-yl | chlorine |
| 1-phenyl-1H-tetrazol-5-yl | chlorine |
| 1-(3-methyl-pyridin-2-yl)-1H-imidazol-2-yl | chlorine |
| 1-(pyridin-2-yl)-1H-imidazol-2-yl | chlorine |

TABLE 9

Compounds of the formula I* where X = S, Y = O, Z = S, A = propylene and with the following further meanings:

| R1 | R2 |
| --- | --- |
| methoxyethoxyethyl | methyl |
| acetyl | methyl |
| 2-pyrimidinyl | methyl |
| 2-benzimidazolyl | methyl |
| H | methyl |
| methyl | methyl |
| methoxyethyl | methyl |
| 1-(4-hydroxyphenyl)-1H-tetrazol-5-yl | methyl |
| 4-pyridyl | methyl |
| 5-methylthio-benzimidazol-2-yl | methyl |
| 5-(thiazol-2-yl)-benzimidazol-2-yl | methyl |
| 5-methylsulfonyl-benzimidazol-2-yl | methyl |
| 1-phenyl-1H-tetrazol-5-yl | methyl |
| 1-(3-methyl-pyridin-2-yl)-1H-imidazol-2-yl | methyl |
| 1-(pyridin-2-yl)-1H-imidazol-2-yl | methyl |
| methoxyethoxyethyl | chlorine |
| acetyl | chlorine |
| 2-pyrimidinyl | chlorine |
| 2-benzimidazolyl | chlorine |
| H | chlorine |
| methyl | chlorine |
| methoxyethyl | chlorine |
| 1-(4-hydroxyphenyl)-1H-tetrazol-5-yl | chlorine |
| 4-pyridyl | chlorine |
| 5-methylthio-benzimidazol-2-yl | chlorine |
| 5-(thiazol-2-yl)-benzimidazol-2-yl | chlorine |
| 5-methylsulfonyl-benzimidazol-2-yl | chlorine |
| 1-phenyl-1H-tetrazol-5-yl | chlorine |
| 1-(3-methyl-pyridin-2-yl)-1H-imidazol-2-yl | chlorine |
| 1-(pyridin-2-yl)-1H-imidazol-2-yl | chlorine |

TABLE 10

Compounds of the formula I* where X = O, Y = N-methyl, Z = S, A = ethylene and with the following further meanings:

| R1 | R2 |
| --- | --- |
| methoxyethoxyethyl | methyl |
| acetyl | methyl |
| 2-pyrimidinyl | methyl |
| 2-benzimidazolyl | methyl |
| H | methyl |
| methyl | methyl |
| methoxyethyl | methyl |
| 1-(4-hydroxyphenyl)-1H-tetrazol-5-yl | methyl |
| 4-pyridyl | methyl |
| 5-methylthio-benzimidazol-2-yl | methyl |
| 5-(thiazol-2-yl)-benzimidazol-2-yl | methyl |
| 5-methylsulfonyl-benzimidazol-2-yl | methyl |
| 1-phenyl-1H-tetrazol-5-yl | methyl |
| 1-(3-methyl-pyridin-2-yl)-1H-imidazol-2-yl | methyl |
| 1-(pyridin-2-yl)-1H-imidazol-2-yl | methyl |
| methoxyethoxyethyl | chlorine |
| acetyl | chlorine |
| 2-pyrimidinyl | chlorine |
| 2-benzimidazolyl | chlorine |
| H | chlorine |
| methyl | chlorine |
| methoxyethyl | chlorine |
| 1-(4-hydroxyphenyl)-1H-tetrazol-5-yl | chlorine |
| 4-pyridyl | chlorine |
| 5-methylthio-benzimidazol-2-yl | chlorine |
| 5-(thiazol-2-yl)-benzimidazol-2-yl | chlorine |
| 5-methylsulfonyl-benzimidazol-2-yl | chlorine |
| 1-phenyl-1H-tetrazol-5-yl | chlorine |
| 1-(3-methyl-pyridin-2-yl)-1H-imidazol-2-yl | chlorine |
| 1-(pyridin-2-yl)-1H-imidazol-2-yl | chlorine |

TABLE 11

Compounds of the formula I* where X = O, Y = N-methyl, Z = S, A = propylene and with the following further meanings:

| R1 | R2 |
| --- | --- |
| methoxyethoxyethyl | methyl |
| acetyl | methyl |
| 2-pyrimidinyl | methyl |
| 2-benzimidazolyl | methyl |
| H | methyl |
| methyl | methyl |
| methoxyethyl | methyl |
| 1-(4-hydroxyphenyl)-1H-tetrazol-5-yl | methyl |
| 4-pyridyl | methyl |
| 5-methylthio-benzimidazol-2-yl | methyl |
| 5-(thiazol-2-yl)-benzimidazol-2-yl | methyl |
| 5-methylsulfonyl-benzimidazol-2-yl | methyl |
| 1-phenyl-1H-tetrazol-5-yl | methyl |
| 1-(3-methyl-pyridin-2-yl)-1H-imidazol-2-yl | methyl |
| 1-(pyridin-2-yl)-1H-imidazol-2-yl | methyl |
| methoxyethoxyethyl | chlorine |
| acetyl | chlorine |
| 2-pyrimidinyl | chlorine |
| 2-benzimidazolyl | chlorine |
| H | chlorine |
| methyl | chlorine |
| methoxyethyl | chlorine |
| 1-(4-hydroxyphenyl)-1H-tetrazol-5-yl | chlorine |
| 4-pyridyl | chlorine |
| 5-methylthio-benzimidazol-2-yl | chlorine |
| 5-(thiazol-2-yl)-benzimidazol-2-yl | chlorine |
| 5-methylsulfonyl-benzimidazol-2-yl | chlorine |
| 1-phenyl-1H-tetrazol-5-yl | chlorine |
| 1-(3-methyl-pyridin-2-yl)-1H-imidazol-2-yl | chlorine |
| 1-(pyridin-2-yl)-1H-imidazol-2-yl | chlorine |

TABLE 12

Compounds of the formula I* where X = O, Y = S, Z = S, A = ethylene and with the following further meanings:

| R1 | R2 |
| --- | --- |
| methoxyethoxyethyl | methyl |
| acetyl | methyl |
| 2-pyrimidinyl | methyl |
| 2-benzimidazolyl | methyl |
| H | methyl |
| methyl | methyl |
| methoxyethyl | methyl |
| 1-(4-hydroxyphenyl)-1H-tetrazol-5-yl | methyl |
| 4-pyridyl | methyl |
| 5-methylthio-benzimidazol-2-yl | methyl |
| 5-(thiazol-2-yl)-benzimidazol-2-yl | methyl |
| 5-methylsulfonyl-benzimidazol-2-yl | methyl |
| 1-phenyl-1H-tetrazol-5-yl | methyl |
| 1-(3-methyl-pyridin-2-yl)-1H-imidazol-2-yl | methyl |
| 1-(pyridin-2-yl)-1H-imidazol-2-yl | methyl |
| methoxyethoxyethyl | chlorine |
| acetyl | chlorine |
| 2-pyrimidinyl | chlorine |
| 2-benzimidazolyl | chlorine |
| H | chlorine |
| methyl | chlorine |
| methoxyethyl | chlorine |
| 1-(4-hydroxyphenyl)-1H-tetrazol-5-yl | chlorine |
| 4-pyridyl | chlorine |
| 5-methylthio-benzimidazol-2-yl | chlorine |
| 5-(thiazol-2-yl)-benzimidazol-2-yl | chlorine |
| 5-methylsulfonyl-benzimidazol-2-yl | chlorine |
| 1-phenyl-1H-tetrazol-5-yl | chlorine |
| 1-(3-methyl-pyridin-2-yl)-1H-imidazol-2-yl | chlorine |
| 1-(pyridin-2-yl)-1H-imidazol-2-yl | chlorine |

TABLE 13

Compounds of the formula I* where X = O, Y = S, Z = S, A = propylene and with the following further meanings:

| R1 | R2 |
|---|---|
| methoxyethoxyethyl | methyl |
| acetyl | methyl |
| 2-pyrimidinyl | methyl |
| 2-benzimidazolyl | methyl |
| H | methyl |
| methyl | methyl |
| methoxyethyl | methyl |
| 1-(4-hydroxyphenyl)-1H-tetrazol-5-yl | methyl |
| 4-pyridyl | methyl |
| 5-methylthio-benzimidazol-2-yl | methyl |
| 5-(thiazol-2-yl)-benzimidazol-2-yl | methyl |
| 5-methylsulfonyl-benzimidazol-2-yl | methyl |
| 1-phenyl-1H-tetrazol-5-yl | methyl |
| 1-(3-methyl-pyridin-2-yl)-1H-imidazol-2-yl | methyl |
| 1-(pyridin-2-yl)-1H-imidazol-2-yl | methyl |
| methoxyethoxyethyl | chlorine |
| acetyl | chlorine |
| 2-pyrimidinyl | chlorine |
| 2-benzimidazolyl | chlorine |
| H | chlorine |
| methyl | chlorine |
| methoxyethyl | chlorine |
| 1-(4-hydroxyphenyl)-1H-tetrazol-5-yl | chlorine |
| 4-pyridyl | chlorine |
| 5-methylthio-benzimidazol-2-yl | chlorine |
| 5-(thiazol-2-yl)-benzimidazol-2-yl | chlorine |
| 5-methylsulfonyl-benzimidazol-2-yl | chlorine |
| 1-phenyl-1H-tetrazol-5-yl | chlorine |
| 1-(3-methyl-pyridin-2-yl)-1H-imidazol-2-yl | chlorine |
| 1-(pyridin-2-yl)-1H-imidazol-2-yl | chlorine |

TABLE 14

Compounds of the formula I* where X = S, Y = S, Z = S, A = ethylene and with the following further meanings:

| R1 | R2 |
|---|---|
| methoxyethoxyethyl | methyl |
| acetyl | methyl |
| 2-pyrimidinyl | methyl |
| 2-benzimidazolyl | methyl |
| H | methyl |
| methyl | methyl |
| methoxyethyl | methyl |
| 1-(4-hydroxyphenyl)-1H-tetrazol-5-yl | methyl |
| 4-pyridyl | methyl |
| 5-methylthio-benzimidazol-2-yl | methyl |
| 5-(thiazol-2-yl)-benzimidazol-2-yl | methyl |
| 5-methylsulfonyl-benzimidazol-2-yl | methyl |
| 1-phenyl-1H-tetrazol-5-yl | methyl |
| 1 (3-methyl-pyridin-2-yl)-1H-imidazol-2-yl | methyl |
| 1-(pyridin-2-yl)-1H-imidazol-2-yl | methyl |
| methoxyethoxyethyl | chlorine |
| acetyl | chlorine |
| 2-pyrimidinyl | chlorine |
| 2-benzimidazolyl | chlorine |
| H | chlorine |
| methyl | chlorine |
| methoxyethyl | chlorine |
| 1-(4-hydroxyphenyl)-1H-tetrazol-5-yl | chlorine |
| 4-pyridyl | chlorine |
| 5-methylthio-benzimidazol-2-yl | chlorine |
| 5-(thiazol-2-yl)-benzimidazol-2-yl | chlorine |
| 5-methylsulfonyl-benzimidazol-2-yl | chlorine |
| 1-phenyl-1H-tetrazol-5-yl | chlorine |
| 1-(3-methyl-pyridin-2-yl)-1H-imidazol-2-yl | chlorine |
| 1-(pyridin-2-yl)-1H-imidazol-2-yl | chlorine |

TABLE 15

Compounds of the formula I* where X = S, Y = S, Z = S, A = propylene and with the following further meanings:

| R1 | R2 |
|---|---|
| methoxyethoxyethyl | methyl |
| acetyl | methyl |
| 2-pyrimidinyl | methyl |
| 2-benzimidazolyl | methyl |
| H | methyl |
| methyl | methyl |
| methoxyethyl | methyl |
| 1-(4-hydroxyphenyl)-1H-tetrazol-5-yl | methyl |
| 4-pyridyl | methyl |
| 5-methylthio-benzimidazol-2-yl | methyl |
| 5-(thiazol-2-yl)-benzimidazol-2-yl | methyl |
| 5-methylsulfonyl-benzimidazol-2-yl | methyl |
| 1-phenyl-1H-tetrazol-5-yl | methyl |
| 1-(3-methyl-pyridin-2-yl)-1H-imidazol-2-yl | methyl |
| 1-(pyridin-2-yl)-1H-imidazol-2-yl | methyl |
| methoxyethoxyethyl | chlorine |
| acetyl | chlorine |
| 2-pyrimidinyl | chlorine |
| 2-benzimidazolyl | chlorine |
| H | chlorine |
| methyl | chlorine |
| methoxyethyl | chlorine |
| 1-(4-hydroxyphenyl)-1H-tetrazol-5-yl | chlorine |
| 4-pyridyl | chlorine |
| 5-methylthio-benzimidazol-2-yl | chlorine |
| 5-(thiazol-2-yl)-benzimidazol-2-yl | chlorine |
| 5-methylsulfonyl-benzimidazol-2-yl | chlorine |
| 1-phenyl-1H-tetrazol-5-yl | chlorine |
| 1-(3-methyl-pyridin-2-yl)-1H-imidazol-2-yl | chlorine |
| 1-(pyridin-2-yl)-1H-imidazol-2-yl | chlorine |

TABLE 16

Compounds of the formula I* where X = O, Y = O, Z = O, A = ethylene and with the following further meanings:

| R1 | R2 |
|---|---|
| 2-hydroxyethyl | methyl |
| 2-carboxyethyl | methyl |
| 2-aminoethyl | methyl |
| 2-dimethylaminoethyl | methyl |
| 2-diethylaminoethyl | methyl |
| 2-acetylaminoethyl | methyl |
| cyclopropylmethyl | methyl |
| 2-oxopropyl | methyl |
| 2,2,2-trifluoroethyl | methyl |
| imidazol-2,4-dion-5-yl | methyl |
| 4,6-dimethylpyrimidin-2-yl | methyl |
| 4-methylpyrimidin-2-yl | methyl |
| 4,6-diaminopyrimidin-2-yl | methyl |
| 4-hydroxy-5-ethoxycarbonylpyrimidin-2-yl | methyl |
| 1-(3-chloropyridin-2-yl)-1H-imidazol-2-yl | methyl |
| 1-(4-chloropyridin-2-yl)-1H-imidazol-2-yl | methyl |
| 1-(3-methoxypyridin-2-yl)-1H-imidazol-2-yl | methyl |
| 1-(4-methoxypyridin-2-yl)-1H-imidazol-2-yl | methyl |
| 2-hydroxyethyl | chlorine |
| 2-carboxyethyl | chlorine |
| 2-aminoethyl | chlorine |
| 2-dimethylaminoethyl | chlorine |
| 2-diethylaminoethyl | chlorine |
| 2-acetylaminoethyl | chlorine |
| cyclopropylmethyl | chlorine |
| 2-oxopropyl | chlorine |
| 2,2,2-trifluoroethyl | chlorine |
| imidazol-2,4-dion-5-yl | chlorine |
| 4,6-dimethylpyrimidin-2-yl | chlorine |
| 4-methylpyrimidin-2-yl | chlorine |
| 4,6-diaminopyrimidin-2-yl | chlorine |
| 4-hydroxy-5-ethoxycarbonylpyrimidin-2-yl | chlorine |
| 1-(3-chloropyridin-2-yl)-1H-imidazol-2-yl | chlorine |

TABLE 16-continued

Compounds of the formula I* where X = O, Y = O, Z = O, A = ethylene and with the following further meanings:

| R1 | R2 |
| --- | --- |
| 1-(4-chloropyridin-2-yl)-1H-imidazol-2-yl | chlorine |
| 1-(3-methoxypyridin-2-yl)-1H-imidazol-2-yl | chlorine |
| 1-(4-methoxypyridin-2-yl)-1H-imidazol-2-yl | chlorine |

TABLE 17

Compounds of the formula I* where X = O, Y = O, Z = O, A = propylene and with the following further meanings:

| R1 | R2 |
| --- | --- |
| 2-hydroxyethyl | methyl |
| 2-carboxyethyl | methyl |
| 2-aminoethyl | methyl |
| 2-dimethylaminoethyl | methyl |
| 2-diethylaminoethyl | methyl |
| 2-acetylaminoethyl | methyl |
| cyclopropylmethyl | methyl |
| 2-oxopropyl | methyl |
| 2,2,2-trifluoroethyl | methyl |
| imidazol-2,4-dion-5-yl | methyl |
| 4,6-dimethylpyrimidin-2-yl | methyl |
| 4-methylpyrimidin-2-yl | methyl |
| 4,6-diaminopyrimidin-2-yl | methyl |
| 4-hydroxy-5-ethoxycarbonylpyrimidin-2-yl | methyl |
| 1-(3-chloropyridin-2-yl)-1H-imidazol-2-yl | methyl |
| 1-(4-chloropyridin-2-yl)-1H-lmidazol-2-yl | methyl |
| 1-(3-methoxypyridin-2-yl)-1H-imidazol-2-yl | methyl |
| 1-(4-methoxypyridin-2-yl)-1H-imidazol-2-yl | methyl |
| 2-hydroxyethyl | chlorine |
| 2-carboxyethyl | chlorine |
| 2-aminoethyl | chlorine |
| 2-dimethylaminoethyl | chlorine |
| 2-diethylaminoethyl | chlorine |
| 2-acetylaminoethyl | chlorine |
| cyclopropylmethyl | chlorine |
| 2-oxopropyl | chlorine |
| 2,2,2-trifluoroethyl | chlorine |
| imidazol-2,4-dion-5-yl | chlorine |
| 4,6-dimethylpyrimidin-2-yl | chlorine |
| 4-methylpyrimidin-2-yl | chlorine |
| 4,6-diaminopyrimidin-2-yl | chlorine |
| 4-hydroxy-5-ethoxycarbonylpyrimidin-2-yl | chlorine |
| 1-(3-chloropyridin-2-yl)-1H-imidazol-2-yl | chlorine |
| 1-(4-chloropyridin-2-yl)-1H-imidazol-2-yl | chlorine |
| 1-(3-methoxypyridin-2-yl)-1H-imidazol-2-yl | chlorine |
| 1-(4-methoxypyridin-2-yl)-1H-imidazol-2-yl | chlorine |

TABLE 18

Compounds of the formula I* where X = S, Y = O, Z = O, A = ethylene and with the following further meanings:

| R1 | R2 |
| --- | --- |
| 2-hydroxyethyl | methyl |
| 2-carboxyethyl | methyl |
| 2-aminoethyl | methyl |
| 2-dimethylaminoethyl | methyl |
| 2-diethylaminoethyl | methyl |
| 2-acetylaminoethyl | methyl |
| cyclopropyimethyl | methyl |
| 2-oxopropyl | methyl |
| 2,2,2-trifluoroethyl | methyl |
| imidazol-2,4-dion-5-yl | methyl |
| 4,6-dimethylpyrimidin-2-yl | methyl |
| 4-methylpyrimidin-2-yl | methyl |
| 4,6-diaminopyrimidin-2-yl | methyl |
| 4-hydroxy-5-ethoxycarbonylpyrimidin-2-yl | methyl |

TABLE 18-continued

Compounds of the formula I* where X = S, Y = O, Z = O, A = ethylene and with the following further meanings:

| R1 | R2 |
| --- | --- |
| 1-(3-chloropyridin-2-yl)-1H-imidazol-2-yl | methyl |
| 1-(4-chloropyridin-2-yl)-1H-imidazol-2-yl | methyl |
| 1-(3-methoxypyridin-2-yl)-1H-imidazol-2-yl | methyl |
| 1-(4-methoxypyridin-2-yl)-1H-imidazol-2-yl | methyl |
| 2-hydroxyethyl | chlorine |
| 2-carboxyethyl | chlorine |
| 2-aminoethyl | chlorine |
| 2-dimethylaminoethyl | chlorine |
| 2-diethylaminoethyl | chlorine |
| 2-acetylaminoethyl | chlorine |
| cyclopropylmethyl | chlorine |
| 2-oxopropyl | chlorine |
| 2,2,2-trifluoroethyl | chlorine |
| imidazol-2,4-dion-5-yl | chlorine |
| 4,6-dimethylpyrimidin-2-yl | chlorine |
| 4-methylpyrimidin-2-yl | chlorine |
| 4,6-diaminopyrimidin-2-yl | chlorine |
| 4-hydroxy-5-ethoxycarbonylpyrimidin-2-yl | chlorine |
| 1-(3-chloropyridin-2-yl)-1H-imidazol-2-yl | chlorine |
| 1-(4-chloropyridin-2-yl)-1H-imidazol-2-yl | chlorine |
| 1-(3-methoxypyridin-2-yl)-1H-imidazol-2-yl | chlorine |
| 1-(4-methoxypyridin-2-yl)-1H-imidazol-2-yl | chlorine |

TABLE 19

Compounds of the formula I* where X = S, Y = O, Z = O, A = propylene and with the following further meanings:

| R1 | R2 |
| --- | --- |
| 2-hydroxyethyl | methyl |
| 2-carboxyethyl | methyl |
| 2-aminoethyl | methyl |
| 2-dimethylaminoethyl | methyl |
| 2-diethylaminoethyl | methyl |
| 2-acetylaminoethyl | methyl |
| cyclopropylmethyl | methyl |
| 2-oxopropyl | methyl |
| 2,2,2-trifluoroethyl | methyl |
| imidazol-2,4-dion-5-yl | methyl |
| 4,6-dimethylpyrimidin-2-yl | methyl |
| 4-methylpyrimidin-2-yl | methyl |
| 4,6-diaminopyrimidin-2-yl | methyl |
| 4-hydroxy-5-ethoxycarbonylpyrimidin-2-yl | methyl |
| 1-(3-chloropyridin-2-yl)-1H-imidazol-2-yl | methyl |
| 1-(4-chloropyridin-2-yl)-1H-imidazol-2-yl | methyl |
| 1-(3-methoxypyridin-2-yl)-1H-imidazol-2-yl | methyl |
| 1-(4-methoxypyridin-2-yl)-1H-imidazol-2-yl | methyl |
| 2-hydroxyethyl | chlorine |
| 2-carboxyethyl | chlorine |
| 2-aminoethyl | chlorine |
| 2-dimethylaminoethyl | chlorine |
| 2-diethylaminoethyl | chlorine |
| 2-acetylaminoethyl | chlorine |
| cyclopropylmethyl | chlorine |
| 2-oxopropyl | chlorine |
| 2,2,2-trifluomethyl | chlorine |
| imidazol-2,4-dion-5-yl | chlorine |
| 4,6-dimethylpyrimidin-2-yl | chlorine |
| 4-methylpyrimidin-2-yl | chlorine |
| 4,6-diaminopyrimidin-2-yl | chlorine |
| 4-hydroxy-5-ethoxycarbonylpyrimidin-2-yl | chlorine |
| 1-(3-chloropyridin-2-yl)-1H-imidazol-2-yl | chlorine |
| 1-(4-chloropyridin-2-yl)-1H-imidazol-2-yl | chlorine |
| 1-(3-methoxypyridin-2-yl)-1H-imidazol-2-yl | chlorine |
| 1-(4-methoxypyridin-2-yl)-1H-imidazol-2-yl | chlorine |

TABLE 20

Compounds of the formula I* where X = O, Y = O, Z = S, A = ethylene and with the following further meanings:

| R1 | R2 |
|---|---|
| 2-hydroxyethyl | methyl |
| 2-carboxyethyl | methyl |
| 2-aminoethyl | methyl |
| 2-dimethylaminoethyl | methyl |
| 2-diethylaminoethyl | methyl |
| 2-acetylaminoethyl | methyl |
| cyclopropylmethyl | methyl |
| 2-oxopropyl | methyl |
| 2,2,2-trifluoroethyl | methyl |
| imidazol-2,4-dion-5-yl | methyl |
| 4,6-dimethylpyrimidin-2-yl | methyl |
| 4-methylpyrimidin-2-yl | methyl |
| 4,6-diaminopyrimidin-2-yl | methyl |
| 4-hydroxy-5-ethoxycarbonylpyrimidin-2-yl | methyl |
| 1-(3-chloropyridin-2-yl)-1H-imidazol-2-yl | methyl |
| 1-(4-chloropyridin-2-yl)-1H-imidazol-2-yl | methyl |
| 1-(3-methoxypyridin-2-yl)-1H-imidazol-2-yl | methyl |
| 1-(4-methoxypyridin-2-yl)-1H-imidazol-2-yl | methyl |
| 2-hydroxyethyl | chlorine |
| 2-carboxyethyl | chlorine |
| 2-aminoethyl | chlorine |
| 2-dimethylaminoethyl | chlorine |
| 2-diethylaminoethyl | chlorine |
| 2-acetylaminoethyl | chlorine |
| cyclopropylmethyl | chlorine |
| 2-oxopropyl | chlorine |
| 2,2,2-trifluoroethyl | chlorine |
| imidazol-2,4-dion-5-yl | chlorine |
| 4,6-dimethylpyrimidin-2-yl | chlorine |
| 4-methylpyrimidin-2-yl | chlorine |
| 4,6-diaminopyrimidin-2-yl | chlorine |
| 4-hydroxy-5-ethoxycarbonylpyrimidin-2-yl | chlorine |
| 1-(3-chloropyridin-2-yl)-1H-imidazol-2-yl | chlorine |
| 1-(4-chloropyridin-2-yl)-1H-imidazol-2-yl | chlorine |
| 1-(3-methoxypyridin-2-yl)-1H-imidazol-2-yl | chlorine |
| 1-(4-metnoxypyridin-2-yl)-1H-imidazol-2-yl | chlorine |

TABLE 21

Compounds of the formula I* where X = O, Y = O, Z = S, A = ethylene and with the following further meanings:

| R1 | R2 |
|---|---|
| 2-hydroxyethyl | methyl |
| 2-carboxyethyl | methyl |
| 2-aminoethyl | methyl |
| 2-dimethylaminoethyl | methyl |
| 2-diethylaminoethyl | methyl |
| 2-acetylaminoethyl | methyl |
| cyclopropylmethyl | methyl |
| 2-oxopropyl | methyl |
| 2,2,2-trifluoroethyl | methyl |
| imidazol-2,4-dion-5-yl | methyl |
| 4,6-dimethylpyrimidin-2-yl | methyl |
| 4-methylpyrimidin-2-yl | methyl |
| 4,6-diaminopyrimidin-2-yl | methyl |
| 4-hydroxy-5-ethoxycarbonylpyrimidin-2-yl | methyl |
| 1-(3-chloropyridin-2-yl)-1H-imidazol-2-yl | methyl |
| 1-(4-chloropyridin-2-yl)-1H-imidazol-2-yl | methyl |
| 1-(3-methoxypyridin-2-yl)-1H-imidazol-2-yl | methyl |
| 1-(4-methoxypyridin-2-yl)-1H-imidazol-2-yl | methyl |
| 2-hydroxyethyl | chlorine |
| 2-carboxyethyl | chlorine |
| 2-aminoethyl | chlorine |
| 2-dimethylaminoethyl | chlorine |
| 2-diethylaminoethyl | chlorine |
| 2-acetylaminoethyl | chlorine |
| cyclopropylmethyl | chlorine |
| 2-oxopropyl | chlorine |
| 2,2,2-trifluoroethyl | chlorine |
| imidazol-2,4-dion-5-yl | chlorine |
| 4,6-dimethylpyrimidin-2-yl | chlorine |
| 4-methylpyrimidin-2-yl | chlorine |
| 4,6-diaminopyrimidin-2-yl | chlorine |
| 4-hydroxy-5-ethoxycarbonylpyrimidin-2-yl | chlorine |
| 1-(3-chloropyridin-2-yl)-1H-imidazol-2-yl | chlorine |
| 1-(4-chloropyridin-2-yl)-1H-imidazol-2-yl | chlorine |
| 1-(3-methoxypyridin-2-yl)-1H-imidazol-2-yl | chlorine |
| 1-(4-methoxypyridin-2-yl)-1H-imidazol-2-yl | chlorine |

TABLE 22

Compounds of the formula I* where X = S, Y = O, Z = S, A = ethylene and with the following further meanings:

| R1 | R2 |
|---|---|
| 2-hydroxyethyl | methyl |
| 2-carboxyethyl | methyl |
| 2-aminoethyl | methyl |
| 2-dimethylaminoethyl | methyl |
| 2-diethylaminoethyl | methyl |
| 2-acetylaminoethyl | methyl |
| cyclopropylmethyl | methyl |
| 2-oxopropyl | methyl |
| 2,2,2-trifluoroethyl | methyl |
| imidazol-2,4-dion-5-yl | methyl |
| 4,6-dimethylpyrimidin-2-yl | methyl |
| 4-methylpyrimidin-2-yl | methyl |
| 4,6-diaminopyrimidin-2-yl | methyl |
| 4-hydroxy-5-ethoxycarbonylpyrimidin-2-yl | methyl |
| 1-(3-chloropyridin-2-yl)-1H-imidazol-2-yl | methyl |
| 1-(4-chloropyridin-2-yl)-1H-imidazol-2-yl | methyl |
| 1-(3-methoxypyridin-2-yl)-1H-imidazol-2-yl | methyl |
| 1-(4-methoxypyridin-2-yl)-1H-imidazol-2-yl | methyl |
| 2-hydroxyethyl | chlorine |
| 2-carboxyethyl | chlorine |
| 2-aminoethyl | chlorine |
| 2-dimethylaminoethyl | chlorine |
| 2-diethylaminoethyl | chlorine |
| 2-acetylaminoethyl | chlorine |
| cyclopropylmethyl | chlorine |
| 2-oxopropyl | chlorine |
| 2,2,2-trifluoroethyl | chlorine |
| imidazol-2,4-dion-5-yl | chlorine |
| 4,6-dimethylpyrimidin-2-yl | chlorine |
| 4-methylpyrimidin-2-yl | chlorine |
| 4,6-diaminopyrimidin-2-yl | chlorine |
| 4-hydroxy-5-ethoxycarbonylpyrimidin-2-yl | chlorine |
| 1-(3-chloropyridin-2-yl)-1H-imidazol-2-yl | chlorine |
| 1-(4-chloropyridin-2-yl)-1H-imidazol-2-yl | chlorine |
| 1-(3-methoxypyridin-2-yl)-1H-imidazol-2-yl | chlorine |
| 1-(4-methoxypyridin-2-yl)-1H-imidazol-2-yl | chlorine |

TABLE 23

Compounds of the formula I* where X = S, Y = O, Z = S, A = propylene and with the following further meanings:

| R1 | R2 |
|---|---|
| 2-hydroxyethyl | methyl |
| 2-carboxyethyl | methyl |
| 2-aminoethyl | methyl |
| 2-dimethylaminoethyl | methyl |
| 2-diethylaminoethyl | methyl |
| 2-acetylaminoeihyl | methyl |
| cyclopropylmethyl | methyl |
| 2-oxopropyl | methyl |

TABLE 23-continued

Compounds of the formula I* where X = S, Y = O, Z = S, A = propylene and with the following further meanings:

| R1 | R2 |
|---|---|
| 2,2,2-trifluoroethyl | methyl |
| imidazol-2,4-dion-5-yl | methyl |
| 4,6-dimethylpyrimidin-2-yl | methyl |
| 4-methylpyrimidin-2-yl | methyl |
| 4,6-diaminopyrimidin-2-yl | methyl |
| 4-hydroxy-5-ethoxycarbonylpyrimidin-2-yl | methyl |
| 1-(3-chloropyridin-2-yl)-1H-imidazol-2-yl | methyl |
| 1-(4-chloropyridin-2-yl)-1H-imidazol-2-yl | methyl |
| 1-(3-methoxypyridin-2-yl)-1H-imidazol-2-yl | methyl |
| 1-(4-methoxypyridin-2-yl)-1H-imidazol-2-yl | methyl |
| 2-hydroxyethyl | chlorine |
| 2-carboxyethyl | chlorine |
| 2-aminoethyl | chlorine |
| 2-dimethylaminoethyl | chlorine |
| 2-diethylaminoethyl | chlorine |
| 2-acetylaminoethyl | chlorine |
| cyclopropylmethyl | chlorine |
| 2-oxopropyl | chlorine |
| 2,2,2-trifluoroethyl | chlorine |
| imidazol-2,4-dion-5-yl | chlorine |
| 4,6-dimethylpyrimidin-2-yl | chlorine |
| 4-methylpyrimidin-2-yl | chlorine |
| 4,6-diaminopyrimidin-2-yl | chlorine |
| 4-hydroxy-5-ethoxycarbonylpyrimidin-2-yl | chlorine |
| 1-(3-chloropyridin-2-yl)-1H-imidazol-2-yl | chlorine |
| 1-(4-chloropyridin-2-yl)-1H-imidazol-2-yl | chlorine |
| 1-(3-methoxypyridin-2-yl)-1H-imidazol-2-yl | chlorine |
| 1-(4-methoxypyridin-2-yl)-1H-imidazol-2-yl | chlorine |

TABLE 24

Compounds of the formula I* where X = O, Y = N-methyl, Z = S, A = ethylene and with the following further meanings:

| R1 | R2 |
|---|---|
| 2-hydroxyethyl | methyl |
| 2-carboxyethyl | methyl |
| 2-aminoethyl | methyl |
| 2-dimethylaminoethyl | methyl |
| 2-diethylaminoethyl | methyl |
| 2-acetylaminoethyl | methyl |
| cyclopropylmethyl | methyl |
| 2-oxopropyl | methyl |
| 2,2,2-trifluoroethyl | methyl |
| imidazol-2,4-dion-5-yl | methyl |
| 4,6-dimethylpyrimidin-2-yl | methyl |
| 4-methylpyrimidin-2-yl | methyl |
| 4,6-diaminopyrimidin-2-yl | methyl |
| 4-hydroxy-5-ethoxycarbonylpyrimidin-2-yl | methyl |
| 1-(3-chloropyridin-2-yl)-1H-imidazol-2-yl | methyl |
| 1-(4-chloropyridin-2-yl)-1H-imidazol-2-yl | methyl |
| 1-(3-methoxypyridin-2-yl)-1H-imidazol-2-yl | methyl |
| 1-(4-methoxypyridin-2-yl)-1H-imidazol-2-yl | methyl |
| 2-hydroxyethyl | chlorine |
| 2-carboxyethyl | chlorine |
| 2-aminoethyl | chlorine |
| 2-dimethylaminoethyl | chlorine |
| 2-diethylaminoethyl | chlorine |
| 2-acetylaminoethyl | chlorine |
| cyclopropylmethyl | chlorine |
| 2-oxopropyl | chlorine |
| 2,2,2-trifluoroethyl | chlorine |
| imidazol-2,4-dion-5-yl | chlorine |
| 4,6-dimethylpyrimidin-2-yl | chlorine |
| 4-methylpyrimidin-2-yl | chlorine |
| 4,6-diaminopyrimidin-2-yl | chlorine |
| 4-hydroxy-5-ethoxycarbonylpyrimidin-2-yl | chlorine |
| 1-(3-chloropyridin-2-yl)-1H-imidazol-2-yl | chlorine |

TABLE 24-continued

Compounds of the formula I* where X = O, Y = N-methyl, Z = S, A = ethylene and with the following further meanings:

| R1 | R2 |
|---|---|
| 1-(4-chloropyridin-2-yl)-1H-imidazol-2-yl | chlorine |
| 1-(3-methoxypyridin-2-yl)-1H-imidazol-2-yl | chlorine |
| 1-(4-methoxypyridin-2-yl)-1H-imidazol-2-yl | chlorine |

TABLE 25

Compounds of the formula I* where X = O, Y = N-methyl, Z = S, A = propylene and with the following further meanings:

| R1 | R2 |
|---|---|
| 2-hydroxyethyl | methyl |
| 2-carboxyethyl | methyl |
| 2-aminoethyl | methyl |
| 2-dimethylaminoethyl | methyl |
| 2-diethylaminoethyl | methyl |
| 2-acetylaminoethyl | methyl |
| cyclopropylmethyl | methyl |
| 2-oxopropyl | methyl |
| 2,2,2-trifluoroethyl | methyl |
| imidazol-2,4-dion-5-yl | methyl |
| 4,6-dimethylpyrimidin-2-yl | methyl |
| 4-methylpyrimidin-2-yl | methyl |
| 4,6-diaminopyrimidin-2-yl | methyl |
| 4-hydroxy-5-ethoxycarbonylpyrimidin-2-yl | methyl |
| 1-(3-chloropyridin-2-yl)-1H-imidazol-2-yl | methyl |
| 1-(4-chloropyridin-2-yl)-1H-imidazol-2-yl | methyl |
| 1-(3-methoxypyridin-2-yl)-1H-imidazol-2-yl | methyl |
| 1-(4-methoxypyridin-2-yl)-1H-imidazol-2-yl | methyl |
| 2-hydroxyethyl | chlorine |
| 2-carboxyethyl | chlorine |
| 2-aminoethyl | chlorine |
| 2-dimethylaminoethyl | chlorine |
| 2-diethylaminoethyl | chlorine |
| 2-acetylaminoethyl | chlorine |
| cyclopropylmethyl | chlorine |
| 2-oxopropyl | chlorine |
| 2,2,2-trifluoroethyl | chlorine |
| imidazol-2,4-dion-2-yl | chlorine |
| 4,6-dimethylpyrimidin-2-yl | chlorine |
| 4-methylpyrimidin-2-yl | chlorine |
| 4,6-diaminopyrimidin-2-yl | chlorine |
| 4-hydroxy-5-ethoxycarbonylpyrimidin-2-yl | chlorine |
| 1-(3-chloropyridin-2-yl)-1H-imidazol-2-yl | chlorine |
| 1-(4-chloropyridin-2-yl)-1H-imidazol-2-yl | chlorine |
| 1-(3-methoxypyridin-2-yl)-1H-imidazol-2-yl | chlorine |
| 1-(4-methoxypyridin-2-yl)-1H-imidazol-2-yl | chlorine |

TABLE 26

Compounds of the formula I* where X = O, Y = S, Z = S, A = ethylene and with the following further meanings:

| R1 | R2 |
|---|---|
| 2-hydroxyethyl | methyl |
| 2-carboxyethyl | methyl |
| 2-aminoethyl | methyl |
| 2-dimethylaminoethyl | methyl |
| 2-diethylaminoethyl | methyl |
| 2-acetylaminoethyl | methyl |
| cyclopropylmethyl | methyl |
| 2-oxopropyl | methyl |
| 2,2,2-trifluoroethyl | methyl |
| imidazol-2,4-dion-5-yl | methyl |
| 4,6-dimethylpyrimidin-2-yl | methyl |
| 4-methylpyrimidin-2-yl | methyl |
| 4,6-diaminopyrimidin-2-yl | methyl |
| 4-hydroxy-5-ethoxycarbonylpyrimidin-2-yl | methyl |

TABLE 26-continued

Compounds of the formula I* where X = O, Y = S, Z = S,
A = ethylene and with the following further meanings:

| R1 | R2 |
|---|---|
| 1-(3-chloropyridin-2-yl)-1H-imidazol-2-yl | methyl |
| 1-(4-chloropyridin-2-yl)-1H-imidazol-2-yl | methyl |
| 1-(3-methoxypyridin-2-yl)-1H-imidazol-2-yl | methyl |
| 1-(4-methoxypyridin-2-yl)-1H-imidazol-2-yl | methyl |
| 2-hydroxyethyl | chlorine |
| 2-carboxyethyl | chlorine |
| 2-aminoethyl | chlorine |
| 2-dimethylaminoethyl | chlorine |
| 2-diethylaminoethyl | chlorine |
| 2-acetylaminoethyl | chlorine |
| cyclopropylmethyl | chlorine |
| 2-oxopropyl | chlorine |
| 2,2,2-trifluoroethyl | chlorine |
| imidazol-2,4-dion-5-yl | chlorine |
| 4,6-dimethylpyrimidin-2-yl | chlorine |
| 4-methylpyrimidin-2-yl | chlorine |
| 4,6-diaminopyrimidin-2-yl | chlorine |
| 4-hydroxy-5-ethoxycarbonylpyrimidin-2-yl | chlorine |
| 1-(3-chloropyridin-2-yl)-1H-imidazol-2-yl | chlorine |
| 1-(4-chloropyridin-2-yl)-1H-imidazol-2-yl | chlorine |
| 1-(3-methoxypyridin-2-yl)-1H-imidazol-2-yl | chlorine |
| 1-(4-methoxypyridin-2-yl)-1H-imidazol-2-yl | chlorine |

TABLE 27

Compounds of the formula I* where X = O, Y = S, Z = S,
A = propylene and with the following further meanings:

| R1 | R2 |
|---|---|
| 2-hydroxyethyl | methyl |
| 2-carboxyethyl | methyl |
| 2-aminoethyl | methyl |
| 2-dimethylaminoethyl | methyl |
| 2-diethylaminoethyl | methyl |
| 2-acetylaminoethyl | methyl |
| cyclopropylmethyl | methyl |
| 2-oxopropyl | methyl |
| 2,2,2-trifluoroethyl | methyl |
| imidazol-2,4-dion-5-yl | methyl |
| 4,6-dimethylpyrimidin-2-yl | methyl |
| 4-methylpyrimidin-2-yl | methyl |
| 4,6-diaminopyrimidin-2-yl | methyl |
| 4-hydroxy-5-ethoxycarbonylpyrimidin-2-yl | methyl |
| 1-(3-chloropyridin-2-yl)-1H-imidazol-2-yl | methyl |
| 1-(4-chloropyridin-2-yl)-1H-imidazol-2-yl | methyl |
| 1-(3-methoxypyridin-2-yl)-1H-imidazol-2-yl | methyl |
| 1-(4-methoxypyridin-2-yl)-1H-imidazol-2-yl | methyl |
| 2-hydroxyethyl | chlorine |
| 2-carboxyethyl | chlorine |
| 2-aminoethyl | chlorine |
| 2-dimethylaminoethyl | chlorine |
| 2-diethylaminoethyl | chlorine |
| 2-acetylaminoethyl | chlorine |
| cyclopropylmethyl | chlorine |
| 2-oxopropyl | chlorine |
| 2,2,2-trifluoroethyl | chlorine |
| imidazol-2,4-dion-5-yl | chlorine |
| 4,6-dimethylpyrimidin-2-yl | chlorine |
| 4-methylpyrimidin-2-yl | chlorine |
| 4,6-diaminopyrimidin-2-yl | chlorine |
| 4-hydroxy-5-ethoxycarbonylpyrimidin-2-yl | chlorine |
| 1-(3-chloropyridin-2-yl)-1H-imidazol-2-yl | chlorine |
| 1-(4-chloropyridin-2-yl)-1H-imidazol-2-yl | chlorine |
| 1-(3-methoxypyridin-2-yl)-1H-imidazol-2-yl | chlorine |
| 1-(4-methoxypyridin-2-yl)-1H-imidazol-2-yl | chlorine |

TABLE 28

Compounds of the formula I* where X = S, Y = S, Z = S,
A = ethylene and with the following further meanings:

| R1 | R2 |
|---|---|
| 2-hydroxyethyl | methyl |
| 2-carboxyethyl | methyl |
| 2-aminoethyl | methyl |
| 2-dimethylaminoethyl | methyl |
| 2-diethylaminoethyl | methyl |
| 2-acetylaminoethyl | methyl |
| cyclopropylmethyl | methyl |
| 2-oxopropyl | methyl |
| 2,2,2-trifluoroethyl | methyl |
| imidazol-2,4-dion-5-yl | methyl |
| 4,6-dimethylpyrimidin-2-yl | methyl |
| 4-methylpyrimidin-2-yl | methyl |
| 4,6-diaminopyrimidin-2-yl | methyl |
| 4-hydroxy-5-ethoxycarbonylpyrimidin-2-yl | methyl |
| 1-(3-chloropyridin-2-yl)-1H-imidazol-2-yl | methyl |
| 1-(4-chloropyridin-2-yl)-1H-imidazol-2-yl | methyl |
| 1-(3-methoxypyridin-2-yl)-1H-imidazol-2-yl | methyl |
| 1-(4-methoxypyridin-2-yl)-1H-imidazol-2-yl | methyl |
| 2-hydroxyethyl | chlorine |
| 2-carboxyethyl | chlorine |
| 2-aminoethyl | chlorine |
| 2-dimethylaminoethyl | chlorine |
| 2-diethylaminoethyl | chlorine |
| 2-acetylaminoethyl | chlorine |
| cyclopropylmethyl | chlorine |
| 2-oxopropyl | chlorine |
| 2,2,2-trifluoroethyl | chlorine |
| imidazol-2,4-dion-5-yl | chlorine |
| 4,6-dimethylpyrimidin-2-yl | chlorine |
| 4-methylpyrimidin-2-yl | chlorine |
| 4,6-diaminopyrimidin-2-yl | chlorine |
| 4-hydroxy-5-ethoxycarbonylpyrimidin-2-yl | chlorine |
| 1-(3-chloropyridin-2-yl)-1H-imidazol-2-yl | chlorine |
| 1-(4-chloropyridin-2-yl)-1H-imidazol-2-yl | chlorine |
| 1-(3-methoxypyridin-2-yl)-1H-imidazol-2-yl | chlorine |
| 1-(4-methoxypyridin-2-yl)-1H-imidazol-2-yl | chlorine |

TABLE 29

Compounds of the formula I* where X = S, Y = S, Z = S,
A = propylene and with the following further meanings:

| R1 | R2 |
|---|---|
| 2-hydroxyethyl | methyl |
| 2-carboxyethyl | methyl |
| 2-aminoethyl | methyl |
| 2-dimethylaminoethyl | methyl |
| 2-diethylaminoethyl | methyl |
| 2-acetylaminoethyl | methyl |
| cyclopropylmethyl | methyl |
| 2-oxopropyl | methyl |
| 2,2,2-trifluoroethyl | methyl |
| imidazol-2,4-dion-5-yl | methyl |
| 4,6-dimethylpyrimidin-2-yl | methyl |
| 4-methylpyrimidin-2-yl | methyl |
| 4,6-diaminopyrimidin-2-yl | methyl |
| 4-hydroxy-5-ethoxycarbonylpyrimidin-2-yl | methyl |
| 1-(3-chloropyridin-2-yl)-1H-imidazol-2-yl | methyl |
| 1-(4-chloropyridin-2-yl)-1H-imidazol-2-yl | methyl |
| 1-(3-methoxypyridin-2-yl)-1H-imidazol-2-yl | methyl |
| 1-(4-methoxypyridin-2-yl)-1H-imidazol-2-yl | methyl |
| 2-hydroxyethyl | chlorine |
| 2-carboxyethyl | chlorine |
| 2-aminoethyl | chlorine |
| 2-dimethylaminoethyl | chlorine |
| 2-diethylaminoethyl | chlorine |
| 2-acetylaminoethyl | chlorine |
| cyclopropylmethyl | chlorine |
| 2-oxopropyl | chlorine |
| 2,2,2-trifluoroethyl | chlorine |

TABLE 29-continued

Compounds of the formula I* where X = S, Y = S, Z = S, A = propylene and with the following further meanings:

| R1 | R2 |
|---|---|
| imidazol-2,4-dion-5-yl | chlorine |
| 4,6-dimethylpyrimidin-2-yl | chlorine |
| 4-methylpyrimidin-2-yl | chlorine |
| 4,6-diaminopyrimidin-2-yl | chlorine |
| 4-hydroxy-5-ethoxycarbonylpyrimidin-2-yl | chlorine |
| 1-(3-chloropyridin-2-yl)-1H-imidazol-2-yl | chlorine |
| 1-(4-chloropyridin-2-yl)-1H-imidazol-2-yl | chlorine |
| 1-(3-methoxypyridin-2-yl)-1H-imidazol-2-yl | chlorine |
| 1-(4-methoxypyridin-2-yl)-1H-imidazol-2-yl | chlorine | and the salts of the compounds of the Tables 1 to 29 and their N-oxides and also the salts of the N-oxides.

The compounds according to the invention can be prepared analogously using the processes described in International Patent Applications WO95/34554 and WO95/115324 or using the starting compounds described there or obtainable analogously. In particular, the compounds according to the invention can be prepared as described in greater detail in the following examples or using analogous process steps and by reaction of analogously obtainable starting compounds.

The following examples illustrate the invention in greater detail without restricting it. M.p. stands for melting point, min for minute(s), h for hour(s), dec. for decomposition, DBU for 1,8-diazabicyclo[5.4.0]undec-7-ene.

EXAMPLES

Starting compounds

A1. [4(3-Mercaptopropylsulfanyl)-3-methylpyridin-2-yl]-methanol

A solution of potassium carbonate (691 g, 5 mol) in 1.5 l of water is treated with 1,3-propanedithiol (432.8 g, 4 mol) under a nitrogen atmosphere and heated to 80° C. A solution of (4-chloro-3-methylpyridin-2-yl)methanol hydrochloride (194.1 g, 1 mol) in 400 ml of water is then added dropwise at this temperature with vigorous stirring during the course of about 2 h. The mixture is additionally stirred at 80 to 85° C. for 18 h and then cooled to room temperature. After separating off the aqueous phase, the organic phase is treated with toluene (1.5 l) and washed with water (2×1 l). The organic phase is then extracted with 2M hydrochloric acid (2 l). The hydrochloric acid phase is concentrated and the residue is recrystallized from isopropanol. 159 g (60%) of the title compound are isolated. The crude product is employed without further purification for the synthesis of the compound of Example 1.

A2. 6-[3-(2-Chloromethyl-3-methylpyridin-4-ylsulfanyl)-propylsulfanyl]-3-nitroimidazo-[1,2-b]pyridazine A solution of 3.6 ml (49.8 mmol) of thionyl chloride in 30 ml of dichloromethane is added dropwise at room temperature to a solution of 15.0 g (38.3 mmol) of {3-methyl-4-[3-(3-nitroimidazo[1,2-b]pyridazin-6-yl-sulfanyl)propylsulfanyl]pyridin-2-yl}methanol in 400 ml of anhydrous dichloromethane and the mixture is then stirred for a further 18 h. It is then cooled to 0° C. and aqueous sodium carbonate solution (100 ml) is cautiously added dropwise. The dichloromethane is distilled off. The suspension is then treated with 400 ml of water and stirred at 0° C. for 30 min. The precipitate is filtered off, washed with water, dried at 40° C. in vacuo and then suspended in 300 ml of acetone. After filtration and drying, 15.3 g (97%) of the title compound are isolated as a beige powder. M.p.: 155–156° C.

B1. 3-(2,3-Dimethyl-1-oxypyridin-4-yloxy)propan-1-ol

A solution of 1,3-propanediol (193 ml, 2.66 mol) in 50 ml of anhydrous dimethylformamide is added dropwise at 0° C. during the course of 2 h to a suspension of sodium hydride (24 g of 80% strength suspension, 0.8 mol) in 110 ml of dimethylformamide. The suspension is then stirred at room temperature for 18 h and subsequently heated to 50° C. 4-Chloro-2,3-dimethylpyridine-1-oxide (84 g, 0.53 mol) is added in portions during the course of 15 minutes. The mixture is then heated to 120° C. with stirring for a further 1.5 h. After cooling to 50° C., methanol (500 ml) is added. The salts are then filtered off and washed with methanol. The filtrate is concentrated by distillation in a high vacuum and the residue is purified by chromatography on silica gel. The following gradient of the eluent is used here: 1) ethyl acetate/methanol/ammonia=19:1:0.6, 2) ethyl acetate/methanol/ammonia=18:3:0.6 and 3) ethyl acetate/methanol/ammonia=15:5:0.4. The fractions of $R_f$=0.25 (ethyl acetate/methanol/ammonia=50:20:1) are concentrated and dissolved a further two times in 250 ml of toluene in each case and concentrated again. 76.2 g (72%) of the title compound are isolated as a pale beige solid. M.p. 72–84° C. The crude product is employed for the further reactions without additional purification.

B2. 3-(2-Hydroxymethyl-3-methylpyridin-4-yloxy)propan-1-ol 47 g (0.24 mol) of 3-(2,3-dimethyl-1-oxypyridin-4-yloxy)propan-1-ol and 176 ml (1.87 mol) of acetic anhydride are heated to 90° C. for 5 h. The excess acetic anhydride is then distilled off. The residue is taken up in 40 ml of water and 100 ml of concentrated hydrochloric acid and heated to 80° C. for 16 h. The solution is then treated at room temperature a total of 3 times with 150 ml of isopropanol in each case and concentrated again in a water-jet vacuum. The precipitate is then filtered off, washed with isopropanol and dried. 32 g of the hydrochloride isolated in this way are suspended in 500 ml of isopropanol, treated with 38 g of potassium carbonate and stirred at 80° C. for 1.5 h. The hot solution is filtered and the filtrate is concentrated to dryness. 26.5 g (56%) of the title compound are isolated as a pale beige solid. M.p.: 65–70° C. The crude product is employed for the further reactions without additional purification.

B3. [4-(3-Chloropropoxy)-3-methylpyridin-2-yl]methanol a) 2-Chloromethyl-4-(3-chloropropoxy)-3-methyl-pyridine A solution of 2.3 ml (31.7 mmol) of thionyl chloride in 5 ml of dichloromethane is added dropwise at 0° C. to a solution of 2.5 g (12.6 mmol) of 3-(2-hydroxymethyl-3-methylpyridin-4-yloxy)propan-1-ol in 20 ml of dichloromethane and the mixture is subsequently stirred at room temperature for a further 16 h. Water (20 ml) is then added, and the mixture is adjusted to pH 8 using sodium bicarbonate solution and extracted with 3×20 ml of dichloromethane. The organic extracts are washed with water, dried over magnesium sulfate and concentrated. The residual oil (2.8 g) is employed in stage b) without further purification.

b) 4-(3-Chloropropoxy)-3-methylpyridin-2-ylmethyl acetate

The oil from stage a) (2.8 g, 11.9 mmol) is heated to 100° C. for 6 h with 20 ml of glacial acetic acid and 2.3 g (23.9 mmol) of potassium acetate. The mixture is then concentrated and the residue is taken up in ethyl acetate (30 ml) and sodium hydrogencarbonate solution (30 ml). The solution is then adjusted to pH 7 using 2M hydrochloric acid and extracted with 3×30 ml of ethyl acetate. The organic extracts are washed with water, dried over magnesium sulfate and concentrated. The residual oil (2.8 g) is employed in stage c) without further purification.

c) [4-(3-Chloropropoxy)-3-methylpyridin-2-yl]methanol

A solution of 2.7 g (10.4 mmol) of the oil from stage b) in 25 ml of methanol is treated with 1.5 g (20.8 mmol) of potassium carbonate and stirred at room temperature for 4 h. The salts are then filtered off and the filtrate is concentrated. The residue is purified by chromatography on silica gel (eluent: ethyl acetate/methanol/ammonia=19:1:0.4). 1.3 g (57%) of the title compound are isolated as a colorless oil which partially crystallizes after standing for a relatively long time. This product is employed directly for the further reaction (Example 15) without additional purification.

B4. 3-Nitro-6-tritylsulfanylimidazo[1,2-b]pyridazine 8.0 g (40.3 mmol) of 6-chloro-3-nitroimidazo[1,2-b]pyridazine, 16.7 g (60.4 mmol) of triphenyl-methanethiol and 16.7 g (120 mmol) of potassium carbonate in 150 ml of dioxane are heated to 90° C. for 5 h under an argon atmosphere. After cooling to room temperature, the mixture is filtered and the filtrate is concentrated. The residue is dissolved in a little ethyl acetate and treated with 100 ml of diisopropyl ether. After 18 h, the crystalline precipitate is filtered off and dried. 12.69 g (72%) of the title compound are isolated. M.p.: 168–170° C.

B5. 3-Nitroimidazo[1,2-b]pyridazine-6-thiol

A solution of 1.0 g (2.28 mmol) of 3-nitro-6-tritylsulfanylimidazo[1,2-b]pyridazine in 10 ml of anhydrous dichloromethane is treated with 0.73 ml (4.56 mmol) of triethylsilane and 1.0 ml (13 mmol) of trifluoroacetic acid under an argon atmosphere and stirred at room temperature for 3 h. 10 ml of 2N sodium hydroxide solution is then added and the mixture is extracted with 3×20 ml of ethyl acetate. The aqueous phase is then adjusted to pH 2 using hydrochloric acid and subsequently extracted with 3×20 ml of ethyl acetate. The organic extracts are washed with 20 ml of water, dried over magnesium sulfate and concentrated. The residue is crystallized by addition of a little diethyl ether. 0.34 g (76%) of the title compound is isolated as a pale yellow solid. M.p. 175–177° C.

C1. 3-Chloro-4-[(2-chloroethyl)methylamino]pyridin-2-ylmethyl acetate 3.0 g (10.3 mmol) of (3-chloro-2-chloromethylpyridin-4-yl)-(2-chloroethyl)methylamine hydrochloride and 3.0 g (31 mmol) of potassium acetate are heated at 100° C. for 27 h in 50 ml of glacial acetic acid. The glacial acetic acid is then distilled off and the residue is taken up in 60 ml of ethyl acetate/water (1:1). The mixture is adjusted to pH 8 using sodium bicarbonate solution and extracted with 3×30 ml of ethyl acetate. The organic extracts are washed with water, dried over magnesium sulfate and concentrated. The residue is purified by chromatography on silica gel (eluent: toluene/ethyl acetate=1:1). The fractions of $R_f$=0.25 are concentrated (yield: 1.84 g, 64%) and employed directly for the synthesis of the compound of Example C2.

C2. {3-Chloro-4-[(2-chloroethyl)methylamino]pyridin-2-yl}methanol 1.83 g of 3-chloro-4-[(2-chloroethyl)-methylamino]-pyridin-2-ylmethyl acetate and 250 mg of potassium carbonate in 20 ml of methanol are stirred at room temperature for 8 h. The mixture is then filtered and the filtrate is concentrated. The residue is triturated with diethyl ether. 1.43 g (92%) of the title compound are isolated as a beige solid. M.p. 91–96° C.

C3. (2-Chloroethyl)-[3-chloro-2-(pyrimidin-2-ylsulfanylmethyl)pyridin-4-yl]methylamine hydrochloride A solution of 5.05 g (19.9 mmol) of (3-chloro-2-chloromethylpyridin-4-yl)-(2-chloroethyl)methylamine and 2.23 g (19.9 mmol) of 2-mercaptopyrimidine in 100 ml of isopropanol is heated under reflux for 1.5 h. It is then cooled to room temperature and concentrated, and the residue is taken up in a little ethyl acetate/methanol (1:1). Ethereal hydrogen chloride solution is then added and the mixture is cooled to 0° C. The precipitate is filtered off, washed with ether and dried. 4.24 g (58%) of the title compound are isolated as a pale beige solid. M.p.: 177–180° C. For the further reactions, the base is liberated from the hydrochloride by extraction with 2N sodium hydroxide solution.

C4. [2-(1H-benzimidazol-2-ylsulfanylmethyl)-3-chloro-pyridin-4-yl]-(2-chloroethylmethylamine dihydrochloride Starting from 1.50 g (7.1 mmol) of (3-chloro-2-chloromethylpyridin-4-yl)-(2-chloroethyl)methylamine and 1.06 g (7.1 mmol) of 2-mercaptobenzimidazole in 40 ml of isopropanol, after crystallization from diisopropyl ether, 2.9 g (98%) of the title compound are obtained by the procedure described in Example C3 as a beige solid. M.p. 202° C. (dec.).

D1. 2-{[2-(1H-benzimidazol-2-ylsulfanylmethyl)-3-chloro-pyridin-4-yl]-methyl-amino}-ethanol a) 2-[(3-Chloro-2-chloromethyl-pyridin-4-yl)-methyl-amino]-ethanol Thionyl chloride (7.4 ml, 101.5 mmol), dissolved in dichloromethane (50 ml), is added dropwise at 4° C. to a solution of (2-[(3-chloro-2-hydroxymethyl-pyridin-4-yl)-methylamino]-ethanol (10.0 g, 46.1 mmol) in dichloromethane (150 ml). The solution is stirred for 1 h at this temperature, triturated with ice water and neutralized with saturated sodium bicarbonate solution. After separation of the organic layer the aqueous phase is extracted with dichloromethane. The combined organic extracts are washed with water, dried over magnesium sulfate and evaporated in vacuo. The residue is employed without additional purification for the synthesis described in step b).

b) 2-{[2-(1H-benzimidazol-2-ylsulfanylmethyl)-3-chloro-pyridin-4-yl]-methyl-amino}-ethanol A solution of 2-[(3-chloro-2-chloromethyl-pyridin-4-yl)-methyl-amino]-ethanol isolated in step a) (10.2 g) and 2-mercapto-benzimidazole (5.8 g, 39 mmol) in 2-propanol (250 ml) is boiled under reflux for 2 h. After cooling to 4° C. the precipitate is filtered, washed with 2-propanol and dried in vacuo. The residue is dissolved in water, adjusted to pH 8 with aqueous sodium bicarbonate solution and extracted with ethyl acetate. The combined organic extracts are washed with water, dried over magnesium sulfate and evaporated in vacuo. The residue is crystallized from ethyl acetate to give the title compound as an off-white solid, 7.9 g (58%). M.p. 132–5° C.

D2. 3-{[2-(1H-benzimidazol-2-ylsulfanylmethyl)-3-chloro-pyridin-4-yl]-methyl-amino}-propanol a) 3-[(3-chloro-2-chloromethyl-pyridin-4-yl)-methyl-amino]-propanol Thionyl chloride (3.5 ml, 47.6 mmol), dissolved in dichloromethane (25 ml), is added dropwise at 4° C. to a solution of 3-[(3-chloro-2-hydroxymethyl-pyridin-4-yl)-methyl-amino]-propanol (5.0 g, 21.6 mmol) in dichloromethane (75 ml). The solution is stirred for 1 h at this temperature, triturated with ice water and neutralized with saturated sodium bicarbonate solution. After separation of the organic layer the aqueous phase is extracted with dichloromethane. The combined organic extracts are washed with water, dried over magnesium sulfate and evaporated in vacua. The residue is employed without additional purification for the synthesis described in step b).

b) 3-{[2-(1H-benzimidazol-2-ylsulfanylmethyl)-3-chloro-pyridin-4-yl]-methyl-amino}-propanol A solution of 3-[(3-chloro-2-chloromethyl-pyridin-4-yl)-methyl-amino]-propanol isolated in step a) (5.3 g) and 2-mercapto-benzimidazole (2.2 g, 14.6 mmol) in 2-propanol (150 ml) is boiled under reflux for 2 h. After cooling to 4° C. the precipitate is filtered, washed with 2-propanol and dried in vacua. The residue is dissolved in water, adjusted to pH 8 with aqueous sodium bicarbonate solution and extracted with ethyl acetate. The combined organic extracts are washed with water, dried over magnesium sulfate and evaporated in vacuo. The residue is crystallized from ethyl acetate to give the title compound as an off-white solid, 3.6 g (46%). M.p. 127–30° C.

D3. 2-[(3-Chloro-2-hydroxymethyl-pyridin-4-yl)-methyl-amino]-ethanol a) 2-[(2-Hydroxymethyl-pyridin-4-yl)-methyl-amino]-ethanol A mixture of (4-chloro-pyridin-2-yl)-methanol (20.0 g, 139 mmol) and 2-methylaminoethanol (11.7 ml, 146 mmol) is stirred for 1 h at 140° C. After cooling to room temperature the viscous oil is employed without additional purification for the synthesis described in step b).

b) 2-[(3-Chloro-2-hydroxymethyl-pyridin-4-yl)-methyl-amino]-ethanol

N-Chlorosuccinimide (25 g, 187 mmol) is added in 5 portions to a solution of 2-[(2-hydroxymethyl-pyridin-4-yl)-methyl-amino]-ethanol (30 g of the crude product isolated in step a), 140 mmol) in acetic acid (170 ml) over a period of 3 h. Stirring is continued for I h and the solvent is evaporated in vacuo. The residue is treated with 6N sodium hydroxide solution and extracted with ethyl acetate. The combined organic extracts are washed with water, dried over magnesium sulfate and evaporated in vacuo. The residue is chromatographed (silica, toluene/dioxane 2:1) to give the title compound as a brown solid. M.p. 49–53° C.

D4. 3-[(3-Chloro-2-hydroxymethyl-pyridin-4-yl)-methyl-amino]-propanol

As described in example D3., the title compound is prepared in two steps starting from (4-chloro-pyridin-2-yl)-methanol (15.3 g, 106 mmol) and 3-methylamino-propanol (10.0 g, 112 mmol) and subsequent chlorination of the crude product with N-chlorosuccinimide (19 g, 143 mmol). Yield: 6.4 g (26%), colourless oil.

Final products

1. {3-Methyl-4-[3-(3-nitroimidazo[1,2-b]pyridazin-6-ylsulfanyl)propylsulfanyl]pyridin-2-yl}methanol 10.9 g of sodium hydride (80% strength suspension) are suspended in 350 ml of tetrahydrofuran under a nitrogen atmosphere. A solution of 73 g (0.31 mol) of [4-(3-mercaptopropylsulfanyl)-3-methylpyridin-2-yl]methanol in tetrahydrofuran (350 ml) is then added dropwise with vigorous stirring at room temperature during the course of 2 h. The suspension is then stirred at room temperature for a further 2.5 h. A solution of 51.6 g (0.26 mol) of 6-chloro-3-nitroimidazo[1,2-b]pyridazine in tetrahydrofuran (1000 ml) is then added dropwise during the course of 3.5 h and the mixture is stirred at room temperature for a further 18 h. The mixture is then cooled to 0° C. and cautiously treated with water (500 ml) with vigorous stirring. The organic solvent is then distilled off. The aqueous residue is diluted with a further 500 ml of water and cooled to 0° C. The beige precipitate is filtered off, washed with water and dried in a high vacuum at 40° C. The crude product is then dissolved in hot toluene (1.2 l) and clarified with activated carbon (25 g) and kieselguhr (15 g). After filtration at boiling heat, the solution is concentrated to 750 ml and treated with diisopropyl ether (1.2 l). For complete precipitation, the suspension is cooled to 0° C. with stirring. The precipitate is filtered off and then dried in vacuo at 40° C. For further purification, the product is suspended in hot methanol (1.2 l) and treated again with diisopropyl ether (500 ml) after cooling to room temperature. After filtration and drying in vacuo, 82 g (80%) of the title compound of m.p. 127–129° C. are isolated.

2. 6-{3-[2-(1H-benzimidazol-2-ylsulfanylmethyl)-3-methylpyridin-4-ylsulfanyl]propylsulfanyl}-3-nitroimidazo[1,2-b]pyridazine hydrochloride A suspension of 6-[3-(2-chloromethyl-3-methylpyridin-4-ylsulfanyl)propylsulfanyl]-3-nitroimidazo[1,2-b]pyridazine (0.39 g, 0.95 mmol) and 2-mercapto-1H-benzimidazole (160 mg, 1.05 mmol) in isopropanol (50 ml) is heated under reflux for 7 h. After cooling to room temperature, the precipitate is filtered off, washed with isopropanol and dried at 40° C. in vacuo. The title compound (0.46 g, 86%) is isolated as a beige solid. M.p. 200–207° C (dec.).

3. 6-{3-[3-Methyl-2-(pyridin-4-ylsulfanylmethyl)-pyridin-4-ylsulfanyl]propylsulfanyl}-3-nitro-imidazo[1,2-b]pyridazine hydrochloride 0.53 g (1.3 mmol) of 6-[3-(2-chloromethyl-3-methylpyridin-4-ylsulfanyl)propylsulfanyl]-3-nitro-imidazo[1,2-b]pyridazine and 0.15 g (1.3 mmol) of 4-mercaptopyridine in 30 ml of isopropanol are reacted as described in Example 2. 0.59 g (87%) of the title compound of m.p. 174–178° C. is isolated.

4. 6-{3-[3-Methyl-2-(pyrimidin-2-ylsulfanylmethyl)-pyridin-4-ylsulfanyl]propyisulfanyl)3-nitro-imidazo[1,2-b]pyridazine A suspension of 6-[3-(2-chloromethyl-3-methylpyridin-4-ylsulfanyl)propylsulfanyl]-3-nitroimidazo[1,2-b]pyridazine (1.23 g, 3.0 mmol), 2-mercaptopyrimidine (330 mg, 2.9 mmol) and triethylamine (335 mg, 3.3 mmol) in isopropanol (100 ml) is heated under reflux for 4.5 h. After cooling, the suspension is stirred at room temperature for a further 18 h and then at 0° C. for 0.5 h. The precipitate is filtered off, washed with isopropanol and dried at 40° C. in vacuo. The crystalline solid is then suspended in water (50 ml) and sodium carbonate solution (10 ml). After filtration and drying in vacuo at 40° C., the title compound is isolated as a pale beige solid. Yield 1.40 g (93%), m.p. 143–147° C.

5. 6-{3-[3-Methyl-2-(5-thiazol-2-yl-1H-benzimidazol-2-ylsulfanylmethyl)pyridin-4-yl -sulfanyl]-propyl-sulfanyl}3-nitroimidazo[1,2-b]pyridazine hydrochloride 0.77 g (1.87 mmol) of 6-[3-(2-chloromethyl-3-methylpyridin-4-ylsulfanyl)propylsulfanyl]-3-nitro-imidazo[1,2-b]pyridazine and 0.35 g (1.5 mmol) of 6-thiazol-2-yl-1H-benzimidazole-2-thiol in 25 ml of isopropanol and 20 ml of dimethylformamide are reacted as described in Example 2. 0.60 g (62%) of the title compound of m.p. 232–234° C. is isolated.

6. 6-{3-[3-Methyl-2-(5-methylsulfanyl-1H-benzimidazol-2-ylsulfanylmethyl)pyridin-4-ylsulfanyl]-propyl-sulfanyl)3-nitroimidazo[1,2-b]pyridazine hydrochloride 0.79 g (1.93 mmol) of 6-[3-(2-chloromethyl-3-methylpyridin-4-ylsulfanyl)propylsulfanyl]-3-nitro-imidazo[1,2-b]pyridazine and 0.41 g (1.1 mmol) of 6-methylsulfanyl-1H-benzoimidazole-2-thiol in 35 ml of isopropanol are reacted as described in Example 2. 0.97 g (97%) of the title compound of m.p. 193–195° C. is isolated.

7. 6-{3-[2-(5-methylsulfonyl-1H-benzimidazol-2-yl-sulfanylmethyl)-3-methylpyridin-4-ylsulfanyl]-propylsulfanyl}-3-nitroimidazo[1,2-b]pyridazine A suspension of 6-[3-(2-chloromethyl-3-methylpyridin-4-ylsulfanyl)propylsulfanyl]-3-nitroimidazo[1,2-b]pyridazine (0.9 g, 2.2 mmol), 6-methylsulfonyl-1H-benzimidazole-2-thiol (0.4 g, 1.75 mmol) in isopropanol (30 ml) and dimethylformamide (10 ml) is heated to 95° C for 6 h. After cooling, the suspension is stirred at room temperature for a further 18 h. The solvent is then distilled off. The residue is taken up in 0.2M sodium hydroxide solution (40 ml) and vigorously stirred (15 min). The precipitate is filtered off, washed with water and dried over potassium hydroxide in vacuo. The solid is then suspended twice in 20 ml of hot methanol in each case. After filtration and drying in vacuo at 40° C., the title compound is isolated as a pale beige solid. Yield 0.91 g (86%), m.p. 155–156° C.

8. 6-{3-[2-(2-Methoxyethylsulfanylmethyl)-3-methyl-pyridin-4-ylsulfanyl]propylsulfanyl}-3-nitro-imidazo[1,2-b]pyridazine fumarate A solution of 1-bromo-2-methoxyethane (0.47 ml, 5 mmol) and potassium thioacetate (0.57 g, 5 mmol) in anhydrous ethanol (10 ml) is stirred at 70° C. under a nitrogen atmosphere for 2 h. 0.95 ml of 30% strength sodium methoxide solution is then added and the mixture is stirred at 70° C. for a further 30 min. The reaction mixture is then added directly to a suspension of 1.0 g (2.4 mmol) of 6-[3-(2-chloromethyl-3-methylpyridin-4-ylsulfanyl) propylsulfanyl]-3-nitroimidazo[1,2-b]pyridazin in 20 ml of isopropanol and stirred at 70° C. for a further 30 min. It is cooled to room temperature, treated with 50 ml of water and extracted with 3×50 ml of ethyl acetate. The organic extracts are washed with 20 ml of water, dried over magnesium sulfate and concentrated. The residue is purified by chromatography on silica gel (eluent: toluene/dioxane=2:1). The fractions of $R_f$=0.17 are collected and concentrated. The residue is taken up in acetone (10 ml) and treated with a hot solution of 165 mg of fumaric acid in 20 ml of acetone. After cooling to 0° C., the title compound is isolated as a beige crystallizate. Yield: 0.47 g (33%), m.p.: 132–134° C.

9. 6-(3-}2-[2-(2-Methoxyethoxy)ethylsulfanylmethyl]-3-methylpyridin-4-ylsulfanyl}-propylsulfanyl)-3-nitroimidazo[1,2-b]pyridazine fumarate Starting from 1-(2-bromoethoxy)-2-methoxyethane (0.8 ml, 5.9 mmol), potassium thioacetate (0.68 g, 5.9 mmol) sodium methoxide (1.12 ml of 30% strength solution), ethanol (12 ml), 6-[3-(2-chloromethyl-3-methylpyridin-4-ylsulfanyl)propyisulfanyl-3-nitroimidazo[1,2-b]pyridazine (1.2 g, 2.9 mmol), isopropanol (25 ml), fumaric acid (150 mg) and acetone (20 ml), the title compound is isolated as the fumarate by the procedure indicated in Example 8. M.p.: 128–129° C.

10. S-{3-methyl-4-[3-(3-nitroimidazo[1,2-b]pyridazin-6-ylsulfanyl)propylsulfanyl]-pyridin-2-ylmethyl} thioacetate A suspension of potassium thioacetate (0.44 g, 3.75 mmol) and potassium carbonate (0.87 g, 6.25 mmol) in 10 ml of dimethylformamide is stirred at room temperature for 30 min and then treated with a solution of 1.03 g (2.5 mmol) of 6-[3-(2-chloromethyl-3-methylpyridin-4-ylsulfanyl) propylsulfanyl]-3-nitroimidazo[1,2-b]pyridazine in 10 ml of dimethylformamide. The suspension is stirred at room temperature for a further 18 h. Water (100 ml) is then added, and the mixture is cooled to 0° C. and filtered. After drying the solid in vacuo at 40° C., it is additionally suspended in hot diisopropyl ether. After cooling to room temperature, the solid is again filtered and dried. 1.02 g (98%) of the title compound are isolated as a pale beige solid. M.p.: 138–140° C.

11. 6-Amino-2-{3-methyl-4-[3-(3-nitroimidazo[1,2-b]-pyridazin-6-ylsulfanyl)propyl-sulfanyl}pyridin-2-yl-methylsulfanyl)3H-pyrimidin-4-one A suspension of 0.7 g (1.7 mmol) of 6-[3-(2-chloromethyl-3-methylpyridin-4-ylsulfanyl) propylsulfanyl]-3-nitroimidazo[1,2-b]pyridazine, 0.275 g (1.7 mmol) of 6-amino-2-mercapto-3H-pyrimidin-4-one monohydrate and 0.18 g (1.7 mmol) of sodium carbonate in 20 ml of isopropanol is heated under reflux for 2.5 h. The suspension is then added to 250 ml of water and stirred at room temperature for 30 min. The precipitate is filtered off, washed with water, dried in a high vacuum and suspended in hot methanol. After filtering and drying again, 0.83 g (94%) of the title compound is isolated as a pale beige solid. M.p.: 244–246° C.

12. {3-Methyl-4-[3-(3-nitroimidazo[1,2-b]pyridazin-6-ylsulfanyl)propylsulfanyl]pyridin-2-ylmethyl}-1-thio-β-D-glycopyranoside A suspension of 0.42 g (2.3 mmol) of 1-thio-β-D-glucopyranose sodium salt and 1.0 g (2.5 mmol) of 6-[3-(2-chloromethyl-3-methylpyridin-4-ylsulfanyl) propylsulfanyl]-3-nitroimidazo-[1,2-b]pyridazine in 20 ml of isopropanol is refluxed under a nitrogen atmosphere for 5 h. The suspension is subsequently stirred at 0° C. for a further 1 h and then filtered. The solid is taken up in water (10 ml) and extracted 3 times with 50 ml of a mixture of dichloromethane and methanol (10:1) in each case. The combined organic extracts are dried over magnesium sulfate and concentrated to a volume of 20 ml. The suspension is then stirred at −15° C. for 30 min. The precipitate is filtered off, washed with dichloromethane and dried In a high vacuum. 0.3 g (23%) of the title compound is isolated as a pale beige solid. M.p. 110–115° C.

13. 6-[3-(2,3-Dimethyl-1-oxypyridin-4-yloxy)propoxy]-3-nitroimidazo[1,2-b]pyridazine Sodium hydride (0.54 g of 80% strength suspension, 18 mmol) is added in portions at room temperature to a suspension of 3-(2,3-dimethyl-1-oxypyridin-4-yloxy)-propan-1-ol (3.26 g, 16.5 mmol) in 275 ml of anhydrous dimethylformamide and the mixture is subsequently stirred for a further 2.5 h. A solution of 6-chloro-3-nitroimidazo[1,2-b]pyridazine (2.98 g, 15 mmol) in 75 ml of dimethylformamide is then added dropwise during the course of 1 h, likewise at room temperature, and the mixture is stirred for a further 16 h. Water (150 ml) is then added dropwise and the tetrahydrofuran is distilled off. 500 ml of water are again added to the residue with vigorous stirring. The precipitate is filtered off, washed with water and dried in vacuo. The filtrate is extracted with ethyl acetate (3×200 ml). The organic extracts are washed with water (150 ml), dried over magnesium sulfate and concentrated. The residue is dissolved in hot methanol (175 ml) together with the dried precipitate, and the solution is clarified with a little active carbon, filtered and cooled to 0° C. The precipitate is filtered off and dried. 3.26 g (60%) of the title compound are isolated as a pale beige solid. M.p.: 213–215° C.

14. 3-Methyl-4-[3-(3-nitroimidazo[1,2-b]pyridazin-6-yl-oxy)propoxy]pyridin-2-ylmethyl acetate 2.7 g (7.5 mmol) of 6-[3-(2,3-dimethyl-1-oxypyridin-4-yloxy)propoxy]-3-nitroimidazo[1,2-b]pyridazine and 7.2 ml (75 mmol) of acetic anhydride are heated to 90° C. for 5 h. After cooling to room temperature, ice water (80 ml) is added and the mixture is then adjusted to pH 9–10 using 6N sodium hydroxide solution. The precipitate is filtered off with suction, washed with water and dried. The residue is dissolved in hot toluene (35 ml), clarified with active carbon, concentrated to a volume of 30 ml and cooled to room temperature. Diisopropyl ether (50 ml) is then added and the mixture is stirred at 0° C. for 1 h. The precipitate is filtered off, washed with diisopropyl ether and dried. 2.29 g (76%) of the title compound are isolated as a pale beige solid. M.p.: 148–151° C.

15. {3-Methyl-4-[3-(3-nitroimidazo[1,2-b]pyridazin-6-ylsulfanyl)propoxy]pyridin-2-yl}-methanol 570 mg (2.9 mmol) of 3-nitroimidazo[1,2-b]pyridazine-6-thiol, 500 mg (2.3 mmol) of [4-(3-chloropropoxy)-3- methylpyridin-2-yl]methanol and 0.4 ml (2.9 mmol) of triethylamine in 10 ml of dimethylformamide are heated to 100° C for 1 h under a nitrogen atmosphere. After cooling to room temperature, water (100 ml) is added and the mixture is extracted with 3×50 ml of ethyl acetate. The residual oil is crystallized from methanol. 600 mg (69%) of the title compound are isolated as a pale beige solid. M.p. 135–136° C.

16. (3-Chloro-4-{methyl-[2-(3-nitroimidazo[1,2-b]pyridazin-6-ylsulfanyl)ethyl]amino}-pyridin-2-yl)-methanol 0.33 g (1.28 mmol) of {3-chloro-4-[(2-chloro-ethyl)methylamino]pyridin-2-yl}methanol and 0.33 g (1.68 mmol) of 3-nitroimidazo[1,2-b]pyridazine-6-thiol are dissolved in 10 ml of anhydrous dimethylformamide under an argon atmosphere, and the solution is treated with 0.25 ml (1.53 mmol) of DBU and then stirred at 50° C for 5 h. It is then cooled to room temperature and diluted with ethyl acetate. The precipitate is filtered off, washed with ethyl acetate and diethyl ether and dried. 0.36 g (71%) of the title compound is isolated as a pale beige solid. M.p. 189–191° C.

17. [2-(1H-Benzimidazol-2-ylsulfanylmethyl)-3-chloropyridin-4-yl]methyl-[2-(3-nitroimidazo[1,2-b]pyridazin-6-ylsulfanyl)ethyl]amine 0.44 g (1.0 mmol) of [2-(1H-benzimidazol-2-ylsulfanylmethyl)-3-chloropyridin-4-yl]-(2-chloroethyl)methyl-amine, 0.24 g (1.2 mmol) of 3-nitroimidazo[1,2-b]pyridazine-6-thiol and 0.52 ml (3.5 mmol) of DBU are reacted in 10 ml of dimethylformamide by the procedure described in Example 16. After crystallization from diisopropyl ether, 0.35 g (66%) of the title compound is obtained as a pale beige solid. M.p. 184–185° C.

18. [3-Chloro-2-(pyrimidin-2-ylsulfanylmethyl)pyridin-4-yl]methyl-12-(3-nitroimidazo-[1,2-b]pyridazin-6-ylsulfanyl)ethyl]amine 0.34 g (1.02 mmol) of (2-chloroethyl)-[3-chloro-2-(pyrimidin-2-ylsulfanylmethyl)pyridin-4-yl]methylamine, 0.20 g (1.02 mmol) of 3-nitroimidazo[1,2-b]pyridazine-6-thiol and 0.15 ml (1.02 mmol) of DBU are reacted in 10 ml of dimethylformamide by the procedure described in Example 16. After crystallization from diisopropyl ether, 0.31 g (62%) of the title compound is obtained as a pale beige solid. M.p. 174–175° C.

19. 6-{3-[3-Methyl-2-(1-phenyl-1H-tetrazol-5-ylsulfanylmethyl)pyridin-4-ylsulfanyl]-propylsulfanyl}-3-nitroimidazo[1,2-b]pyridazine hydrochloride 0.61 g (1.5 mmol) of 6-[3-(2-chloromethyl-3-methylpyridin-4-ylsulfanyl)propylsulfanyl]-3-nitro-imidazo[1,2-b]pyridazine and 0.275 g (1.5 mmol) of 1-phenyl-1H-tetrazole-5-thiol in 30 ml of isopropanol are heated under reflux for 2 h under a nitrogen atmosphere. The mixture is then cooled to 0° C., stirred for a further 0.5 h and then filtered. The precipitate is washed with isopropanol and dried in vacuo. 0.84 g (95%) of the title compound is isolated as a pale beige solid. M.p. 204–207° C.

20. 4-(5-{3-Methyl-4-[3-(3-nitroimidazo[1,2-b]pyridazin-6-ylsulfanyl)propylsulfanyl]-pyridin-2-yl-methylsulfanyl)tetrazol-1-yl)phenol 0.61 g (1.5 mmol) of 6-[3-(2-chloromethyl-3-methylpyridin-4-ylsulfanyl)propylsulfanyl]-3-nitroimidazo[1,2-b]pyridazine and 0.30 g (1.5 mmol) of 4-(5-mercaptotetrazol-1-yl)phenol in 30 ml of isopropanol are heated under reflux for 2 h under a nitrogen atmosphere. The mixture is then concentrated. The residue is taken up in 30 ml of water, adjusted to pH 9 using 2N sodium hydroxide solution and extracted with 4×30 ml of dichloromethane. The organic extracts are washed with water, dried over magnesium sulfate and concentrated. The residue is taken up in 200 ml of hot acetonitrile, clarified with active carbon, filtered, concentrated to a volume of 50 ml and cooled to 0° C. The precipitate is filtered off, washed with acetonitrile and dried. 0.64 g (75%) of the title compound is isolated as a pale beige solid. M.p. 92° C. (dec.).

21. 6-(3-(3-Methyl-2-[1-(3-methylpyridin-2-yl)-1H-imidazol-2-ylsulfanylmethyl]pyridin-4-ylsulfanyl}-propylsulfanyl)-3-nitroimidazo[1,2-b]pyridazine hydrochloride 2.13 g (5.2 mmol) of 6-[3-(2-chloromethyl-3-methylpyridin-4-ylsulfanyl)propylsulfanyl]-3-nitroimidazo[1,2-b]pyridazine and 1.0 g (5.2 mmol) of 1-(3-methyl-pyridin-2-yl)-1H-imidazole-2-thiol in 100 ml of isopropanol are heated under reflux for 3 h under a nitrogen atmosphere. The mixture is then cooled to 0° C., stirred for a further 0.5 h and then filtered. The precipitate is taken up in 75 ml of hot water, clarified with active carbon, filtered hot and concentrated to dryness. The residue is crystallized from isopropanol, filtered and dried in vacuo. 1.44 g (45%) of the title compound are isolated as a pale beige solid. M.p. 180–182° C.

22. 6-{3-[3-Methyl-2-(1-pyridin-2-yl-1H-imidazol-2-ylsulfanylmethyl) pyridin-4-yl-sulfanyl]propyl-sulfanyl}3-nitroimidazo[1,2-b]pyridazine 2.3 g (5.6 mmol) of 6-[3-(2-chloromethyl-3-methylpyridin-4-ylsulfanyl)propylsulfanyl]-3-nitroimidazo[1,2-b]pyridazine and 1.0 g (5.6 mmol) of 1-pyridin-2-yl-1H-imidazole-2-thiol in 100 ml of isopropanol are heated under reflux for 2 h under a nitrogen atmosphere. The mixture is then cooled to room temperature, treated with 1 l of water and extracted with 4×200 ml of ethyl acetate. The organic extracts are washed with water, dried over magnesium sulfate and concentrated. The residue is purified by chromatography on silica gel (eluent: ethyl acetate/methanol/ammonia=19:1:0.6). The fractions of $R_f$=0.35 are concentrated and crystallized from methanol. 0.45 g of the title compound is isolated as a pale beige solid. M.p. 146–149° C.

23. 6-[3-(2-Methoxymethyl-3-methylpyridin-4-ylsulfanyl)-propylsulfanyl]-3-nitroimidazo[1,2-b]pyridazine A solution of sodium methanolate (0.69 ml of a 30% strength solution) is added to a suspension of 6-[3-(2-chloromethyl-3-methylpyridin-4-ylsulfanyl)-propylsulfanyl]-3-nitroimidazo[1,2-b]pyridazine (1.23 g, 3 mmol) in methanol (75 ml). After heating under reflux for 16 h and cooling to room temperature the solvent is evaporated in vacuo. The residue is chromatographed (silica, toluene/dioxane 5:1) and crystallized from diisopropylether/ethyl acetate to give the title compound as off-white crystals, 0.34 g (28 %). M.p. 107–110° C.

24. 6-{3-[2-(4,6-Dimethyl-pyrimidin-2-ylsulfanylmethyl)-3-methyl-pyridin-4-ylsulfanyl]-propylsulfanyl}-3-nitroimidazo[1,2-b]pyridazine A suspension of 4,6-dimethyl-pyrimidine-2-thiol (0.35 g, 2.5 mmol) and 6-[3-(2-chloromethyl-3-methyl-pyridin-4-ylsulfanyl)-propylsulfanyl]-3-nitroimidazo[1,2-b]pyridazine (1.03 g, 2.5 mmol) in 2-propanol (50 ml) is heated under reflux for 4 h under a nitrogen atmosphere. After cooling, the mixture is treated with ice water (100 ml), adjusted to pH 10 with 40% strength sodium hydroxide solution, and extracted with ethyl acetate. The combined extracts are washed with sodium carbonate solution, dried over magnesium sulfate and evaporated in vacuo. The residue is crystallized from acetonitrile to give the title compound as a colourless solid, 0.93 g (76%). M.p. 145–7° C.

25. 6-{3-[3-Methyl-2-(4-methyl-pyrimidin-2-ylsulfanylmethyl)-pyridin-4-ylsulfanyl]-propylsulfanyl}-3-nitroimidazo[1,2-b]pyridazine A suspension of 4-methyl-pyrimidine-2-thiol hydrochloride (0.46 g, 2.8 mmol) and 6-[3-(2-chloromethyl-3-methyl-pyridin-4-ylsulfanyl)-propylsulfanyl]-3-nitroimidazo[1,2-b]pyridazine (1.03 g, 2.5 mmol) in 2-propanol (50 ml) is heated under reflux for 4 h under a nitrogen atmosphere. After cooling, the mixture is treated with ice water (100 ml), adjusted to pH 10 with 40% strength sodium hydroxide solution, and extracted with ethyl acetate. The combined extracts are washed with sodium carbonate solution, dried over magnesium sulfate and evaporated in vacuo. The residue is chromatographed (silica, toluene/dioxane 2:1) and crystallized from acetonitrile to give the title compound as a colourless solid, 0.49 g (39%). M.p. 136–8° C.

26. 2-{3-Methyl-4-[3-(3-nitroimidazo[1,2-b]pyridazin-6-ylsulfanyl)-propylsulfanyl]-pyridin-2-ylmethyl-sulfanyl}-pyrimidine-4,6-diamine hydrochloride A suspension of 4,6-diamino-pyrimidine-2-thiol (0.36 g, 2.5 mmol) and 6-[3-(2-chloromethyl-3-methyl-pyridin-4-ylsulfanyl)-propylsulfanyl]-3-nitroimidazo[1,2-b]pyridazine (1.03 g, 2.5 mmol) in 2-propanol (50 ml) is heated under reflux for 6 h under a nitrogen atmosphere. After cooling to 4° C., the precipitate is filtered, washed with cold 2-propanol and dried in vacuo. The crude product is triturated with hot acetonitrile (15 ml), filtered and dried again in vacuo to give the title compound as an off-white solid, 1.25 g (90%). M.p. 215–224° C.

27. [2-(1H-benzimidazol-2-ylsulfanylmethyl)-3-chloropyridin-4-yl]-methyl-[2-(3-nitroimidazo[1,2-b]pyridazin-6-yloxy)-ethyl]amine hydrochloride A solution of 2-{[2-(1H-benzimidazol-2-ylsulfanylmethyl)-3-chloropyridin-4-yl]-methylamino}-ethanol (7.5 g, 21.5 mmol) in dimethylformamide (75 ml) is treated with sodium hydride (1.4 g 80% strength suspension) and stirred for 1 h at room temperature. Then 6-chloro-3-nitro-imidazo[1,2-b]pyridazine (4.3 g, 21.5 mmol) in tetrahydrofurane (50 ml) is added dropwise over a period of 20 min and stirring is continued for another 2 h. The solution is treated with water (750 ml) and extracted extensively with ethyl acetate. The combined organic extracts are washed with water, dried over magnesium sulfate and evaporated in vacuo. The residue is chromatographed (silica, toluene/dioxane/ammonia 2:1:0.1) and crystallized from ethyl acetate. The crude product is dissolved in boiling 2-pronanol (250 ml) and treated with charcoal. After filtration and cooling to 35° C., a saturated solution of hydrogen chloride in diethyl ether (1.5 ml) is added and the mixture is cooled to 4° C. The precipitate is filtered, washed with 2-propanol and dried in vacuo to give the title compound as a faintly yellow solid, 3.6 g (31%). M.p. 211–2° C.

28. [2-(1H-benzimidazol-2-ylsulfanylmethyl)-3-chloropyridin-4-yl]-methyl-[3-(3-nitroimidazo[1,2-b]pyridazin-6-yloxy)-propyl]amine hydrochloride Starting from 3-{[2-(1H-benzimidazol-2-ylsulfanylmethyl)-3-chloropyridin-4-yl]-methylamino}-propan-1-ol (3.0 g, 8.2 mmol) (see example D2.), 6-chloro-3-nitro-imidazo[1,2-b]pyridazine (1.72 g, 8.7 mmol) and sodium hydride (0.62 g 80% strength suspension) the title compound is prepared and purified according to the procedure given for example 27. Yield: 1.95 g, (42%). M.p. 202–03° C.

Commercial Utility

The excellent activity of compounds of the formula I and their salts against Helicobacter bacteria permits their use in human medicine as active compounds for the treatment of diseases which are based on Helicobacter bacteria.

The invention therefore further relates to a method for the treatment of mammals, in particular humans, who are suffering from diseases which are based on Helicobacter bacteria. The method comprises administering to the sick individual a therapeutically active and pharmacologically tolerable amount of one or more compounds of the formula I and/or their pharmacologically tolerable salts.

The invention additionally relates to the compounds of the formula I and their pharmacologically tolerable salts for use in the treatment of diseases which are based on Helicobacter bacteria.

The invention likewise comprises the use of compounds of the formula I and their pharmacologically tolerable salts in the production of medicaments which are employed for the control of those diseases which are based on Helicobacter bacteria.

The invention furthermore relates to medicaments for the control of Helicobacter bacteria, which contain one or more compounds of the general formula I and/or their pharmacologically tolerable salts.

Of the Helicobacter strains against which the compounds of the formula I have proven effective, the strain *Helicobacter pylori* may be mentioned in particular.

The medicaments are prepared by methods known per se and familiar to the person skilled in the art. As medicament, the pharmacologically active compounds of the formula I and their salts (=active compounds) are either employed as such, or preferably in combination with suitable pharmaceutical auxiliaries, e.g. in the form of tablets, coated tablets, capsules, emulsions, suspensions, gels or solutions, the active compound content preferably being between 0.1 and 95%.

The person skilled in the art is familiar on the basis of his expert knowledge with the auxiliaries which are suitable for the desired pharmaceutical formulations. Beside solvents, gel-forming agents, tablet auxiliaries and other active compound vehicles, it is possible to use, for example, antioxidants, dispersants, emulsifiers, antifoams, flavor corrigents, preservatives, stabilizers, colorants or permeation promoters and complexing agents (e.g. cyclodextrins).

The active compounds can be administered, for example, parenterally (e.g. intravenously) or in particular orally.

In general, in human medicine the active compounds are administered in a daily dose from approximately 0.2 to 50, preferably 1 to 30, mg/kg of body weight, if appropriate in the form of several, preferably 2 to 6, individual doses to achieve the desired result.

The compounds according to the invention can also be administered in fixed or free combination together with a substance neutralizing gastric acid and/or inhibiting gastric acid secretion and/or with a substance suitable for the conventional control of *Helicobacter pylori*.

Substances neutralizing gastric acid which may be mentioned are, for example, sodium hydrogencarbonate or other antacids (such as aluminum hydroxide, magnesium aluminate or magaldrate). Substances inhibiting gastric acid secretion which may be mentioned are, for example, $H_2$ blockers (e.g. cimetidine, ranitidine), $H^+/K^+$ ATPase inhibitors (e.g. lansoprazole, omeprazole or in particular pantoprazole) and also so-called peripheral anticholinergics (e.g. pirenzepine, telenzepine).

Substances suitable for the conventional control of *Helicobacter pylori* which may be mentioned are, in particular, antimicrobially active substances such as, for example, penicillin G, gentamycin, erythromycin, clarithromycin, nitrofurazone, tinidazole, nitrofurantoin, furazoli-done, metronidazole and amoxycillin, or else also bismuth salts such as, for example, bismuth citrate.

Biological Investigations

The compounds of the formula I were investigated with respect to their activity against *Helicobacter pylori* following the methodology described by Tomoyuki Iwahi et al. (Antimicrobial Agents and Chemotherapy, 1991, 490–496) using Columbia agar (Oxoid) and with a growth period of 4 days. The approx. MIC 50 values listed in Table A below resulted here for the compounds investigated (the stated numbers of the compounds agree with the example numbers in the description).

With respect to their in vivo activity against Helicobacter fells in the mouse, the compounds of the formula I were investigated following the methodology described by E. Dick-Hegedus and A. Lee (Scand. J. Gastroenterol. 1991, 26, 909–915). The substances were administered orally at 3×50 mg/kg over the course of 4 days. The elimination rates listed in Table A below resulted here for the compounds investigated:

TABLE A

| Compound | MIC50, mg/l | % Elimination |
|---|---|---|
| 1 | 0.05 | 100 |
| 4 | 0.1 | 100 |
| 9 | 0.1 | 100 |
| 13 | 0.5 | 100 |
| 15 | 0.05 | 100 |
| 17 | 0.1 | 100 |
| 18 | 0.1 | 100 |
| 25 | 0.05 | 100 |
| 27 | 0.1 | 100 |

I claim:
1. A compound of the formula I

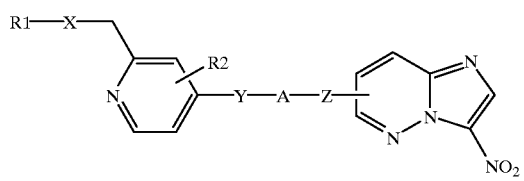

(I)

in which
R1 is hydrogen, 1–4C-alkyl, 1–4C-alkyl substituted by R11, 1–4C-alkylcarbonyl, 1–4C-alkoxycarbonyl, sulfo (—SO₃H) or a cyclic system or bicyclic system substituted by R11 and R12, which is selected from the group consisting of pyrrole, furan, thiophene, pyrazole, imidazole, imidazoline, oxazole, isoxazole, thiazole, thiazoline, isothiazole, triazole, oxadiazole, thiadiazole, thiadiazole-1-oxide, tetrazole, hexopyranoses, benzene, pyridine, pyridine-N-oxide, pyridazine, pyrimidine, pyrazine, triazine, naphthalene, quinoline, quinazoline, quinoxaline, benzimidazole, benzoxazole, benzothiazole, thiazolopyridine and imidazopyridine,
where
R11 is hydrogen, 1–4C-alkyl, 3–7C-cycloalkyl, 1–4C-alkoxy, 1–4C-alkoxy-1–4C-alkoxy, 1–4C-alkylcarbonyl, amino, 1–4C-alkylcarbonylamino, halogen, trifluoromethyl, trifluoromethoxy, hydroxyl, carboxyl, 1–4C-alkoxycarbonyl, 1–4C-alkylthio, 1–4C-alkylsulfinyl, 1–4C-alkylsulfonyl, sulfo (—SO₃H), nitro, guanidino, phenyl, phenyl substituted by R111, pyridyl, pyridyl substituted by R111, imidazolyldione, thiazolyl, 1–4C-alkyl substituted by R111, —N(R112)R113 or —CO—N(R112)R113 and
R12 is hydrogen, 1–4C-alkyl, 1–4C-alkoxy, halogen, amino, hydroxyl, phenyl or trifluoromethyl,
where
R111 is hydroxyl, 1–4C-alkyl, 1–4C-alkoxy, carboxyl, 1–4C-alkoxycarbonyl, halogen, aminosulfonyl or —N(R112)R113,
R112 is hydrogen, 1–4C-alkyl, formyl, 1–4C-alkylcarbonyl or 1–4C-alkoxycarbonyl and
R113 is hydrogen or 1–4C-alkyl, or where
R112 and R113, together and including the nitrogen atom to which both are bonded, are a piperidino or morpholino radical,
R2 is hydrogen, 1–4C-alkyl or halogen,
A is 2–7C-alkylene,
X is a bonding dash, O (oxygen) or S (sulfur),
Y is O (oxygen), S (sulfur) or N-1–4C-alkyl and
Z is O (oxygen) or S (sulfur), or a salt of this compound, its N-oxide or the salts of the N-oxides.

2. A compound as claimed in claim 1, of formula I*

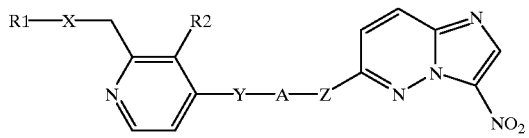

(I*)

in which
R1, R2, A, X, Y and Z have the meanings indicated in claim 1,
or a salt of this compound, its N-oxide or the salts of the N-oxides.

3. A compound of formula I as claimed in claim 1, in which
R1 is hydrogen, 1–4C-alkyl, 1–4C-alkyl substituted by R11, 1–4C-alkylcarbonyl, sulfo (—SO₃H) or a cyclic system or bicyclic system substituted by R11 and R12, which is selected from the group consisting of pyrrole, furan, thiophene, pyrazole, imidazole, imidazoline, oxazole, isoxazole, thiazole, thiazoline, isothiazole, triazole, oxadiazole, thiadiazole, thiadiazole-1-oxide, tetrazole, hexopyranoses, benzene, pyridine, pyridine-N-oxide, pyridazine, pyrimidine, pyrazine, naphthalene, quinoline, quinazoline, quinoxaline, benzimidazole, benzothiazole, thiazolopyridine and imidazopyridine,
where
R11 is hydrogen, 1–4C-alkyl, 3–7C-cycloalkyl, 1–4C-alkoxy, 1–4C-alkoxy-1–4C-alkoxy, 1–4C-alkylcarbonyl, amino, 1–4C-alkylcarbonylamino, halogen, trifluoromethyl, trifluoromethoxy, hydroxyl, carboxyl, 1–4C-alkoxycarbonyl, 1–4C-alkylthio, 1–4C-alkylsulfonyl, nitro, phenyl, phenyl substituted by R111, pyridyl, pyridyl substituted by R111, imidazolyldione, thiazolyl, 1–4C-alkyl substituted by R111, —N(R112)R113 or —CO—N(R112)R113 and R12 is hydrogen, 1–4C-alkyl, 1–4C-alkoxy, halogen, amino, hydroxyl or phenyl,
where
R111 is hydroxyl, 1–4C-alkyl, 1–4C-alkoxy, carboxyl, halogen, aminosulfonyl or —N(R112)R113,
R112 is hydrogen, 1–4C-alkyl, 1–4C-alkylcarbonyl or i-4C-alkoxycarbonyl and
R113 is hydrogen or 1–4C-alkyl,
R2 is hydrogen, 1–4C-alkyl or halogen,
A is 2–7C-alkylene,
X is a bonding dash, O (oxygen) or S (sulfur),
Y is O (oxygen), S (sulfur) or N-1–4C-alkyl and
Z is O (oxygen) or S (sulfur),
or a salt of this compound, its N-oxide or the salts of the N-oxides.

4. A compound of the formula I as claimed in claim 1, in which
R1 is hydrogen, 1–4C-alkyl, 1–4C-alkyl substituted by R11, 1–4C-alkylcarbonyl, sulfo (—SO₃H) or a cyclic system or bicyclic system substituted by R11 and R12, which is selected from the group consisting of imidazole, tetrazole, hexopyranoses, pyridine, pyridine-N-oxide, pyrimidine, benzimidazole and thiazolopyridine,
where
R11 is hydrogen, 1–4C-alkyl, 3–7C-cycloalkyl, 1–4C-alkoxy, 1–4C-alkoxy-1–4C-alkoxy, 1–4C-alkylcarbonyl, amino, halogen, trifluoromethyl, hydroxyl, carboxyl, 1–4C-alkoxycarbonyl, 1–4C-alkylthio, 1–4C-alkylsulfonyl, phenyl, phenyl substituted by R111, pyridyl, pyridyl substituted by R111, imidazolyidione, thiazolyl, 1–4C-alkyl substituted by R111 or —N(R112)R113 and
R12 is hydrogen, 1–4C-alkyl, amino or hydroxyl,
where
R111 is hydroxyl, 1–4C-alkyl, 1–4C-alkoxy or —N(R112)R113,
R112 is hydrogen, 1–4C-alkyl or 1–4C-alkylcarbonyl and
R113 is hydrogen or 1–4C-alkyl,
R2 is hydrogen, 1–4C-alkyl or halogen,
A is 2–5C-alkylene,
X is a bonding dash, O (oxygen) or S (sulfur),
Y is O (oxygen), S (sulfur) or N-1–4C-alkyl and
Z is O (oxygen) or S (sulfur),
or a salt of this compound, its N-oxide or the salts of the N-oxides.

5. A compound as claimed in claim 1, of formula I*

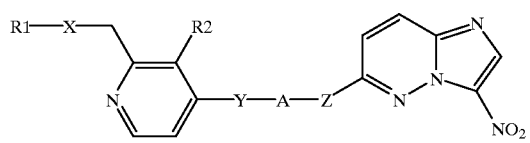

(I*)

in which
R1 is hydrogen, 1–4C-alkyl, 1–4C-alkyl substituted by R11, 1–4C-alkylcarbonyl, sulfo (—SO₃H) or a cyclic system or bicyclic system substituted by R11 and R12, which is selected from the group consisting of imidazole, tetrazole, pyridine, pyrimidine and benzimidazole,
where
R11 is hydrogen, 1–4C-alkyl, 1–4C-alkoxy, 1–4C-alkoxy-1–4C-alkoxy, 1–4C-alkylthio, 1–4C-alkylsulfonyl, phenyl, phenyl substituted by R111, pyridyl, pyridyl substituted by R111 or thiazolyl and
R12 is hydrogen,
where
R11 is hydroxyl or 1–4C-alkyl,
R2 is 1–4C-alkyl or halogen,
A is 2–4C-alkylene,
X is a bonding dash, O (oxygen) or S (sulfur),
Y is O (oxygen), S (sulfur) or N-1–4C-alkyl and
Z is O (oxygen) or S (sulfur),
or a salt of this compound, its N-oxide or the salts of the N-oxides.

6. A compound as claimed in claim 1, of formula I*

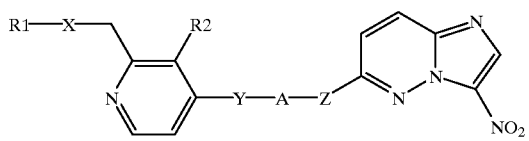

(I*)

in which
R1 is benzimidazol-2-yl,
R2 is 1–4C-alkyl or halogen,
A is 2–4C-alkylene,
X is a bonding dash, O (oxygen) or S (sulfur),
Y is O (oxygen), S (sulfur) or N-1–4C-alkyl and
Z is O (oxygen) or S (sulfur),
or a salt of this compound, its N-oxide or the salts of the N-oxides.

7. A compound of the formula I as claimed in claim 1, in which X is S (sulfur), Y is S (sulfur) and Z is S (sulfur).

8. A compound of the formula I as claimed in claim 1, in which A is 2–4C-alkylene, X is S (sulfur), Y is N-1–4C-alkyl and Z is O (oxygen).

9. A medicament comprising an effective amount of a compound of claim 1 together with a customary pharmaceutical auxiliary or excipient.

10. In a method for controlling Helicobacter bacteria with an active ingredient, the improvement wherein the active ingredient is a compound as claimed in claim 1.

11. In a method for treating a mammal afflicted with a disease based on Helicobacter bacteria with an active ingredient, the improvement wherein the active ingredient is a pharmacologically-acceptable compound as claimed in claim 1.

* * * * *